US007250416B2

(12) United States Patent
Phiasivongsa et al.

(10) Patent No.: US 7,250,416 B2
(45) Date of Patent: Jul. 31, 2007

(54) AZACYTOSINE ANALOGS AND DERIVATIVES

(75) Inventors: Pasit Phiasivongsa, Brentwood, CA (US); Sanjeev Redkar, Hayward, CA (US)

(73) Assignee: SuperGen, Inc., Dublin, CA (US)

( * ) Notice: Subject to any disclaimer, the term of this patent is extended or adjusted under 35 U.S.C. 154(b) by 0 days.

(21) Appl. No.: 11/077,862

(22) Filed: Mar. 11, 2005

(65) Prior Publication Data

US 2006/0205685 A1   Sep. 14, 2006

(51) Int. Cl.
*C07D 251/48* (2006.01)
*C07H 19/048* (2006.01)
*A61K 31/53* (2006.01)
*A61K 31/7052* (2006.01)
*A61P 35/00* (2006.01)

(52) U.S. Cl. .................. 514/241; 544/205; 544/206; 544/218; 544/220

(58) Field of Classification Search ............... 544/205, 544/206, 218, 220, 241; 514/241
See application file for complete search history.

(56) References Cited

U.S. PATENT DOCUMENTS

| | | | |
|---|---|---|---|
| 4,690,918 | A | 9/1987 | Beppu et al. |
| 5,736,531 | A | 4/1998 | Von Borstel et al. |
| 5,856,090 | A | 1/1999 | Epstein |
| 5,968,914 | A | 10/1999 | Von Borstel et al. |
| 6,136,791 | A | 10/2000 | Nyce |
| 6,432,924 | B1 | 8/2002 | Nyce |
| 2001/0012835 | A1 | 8/2001 | Fine et al. |
| 2002/0114809 | A1 | 8/2002 | Rubinfeld et al. |
| 2003/0039689 | A1 | 2/2003 | Chen et al. |
| 2003/0045497 | A1 | 3/2003 | Widegren et al. |
| 2003/0108588 | A1 | 6/2003 | Chen et al. |
| 2003/0147813 | A1 | 8/2003 | Lyons |
| 2003/0158598 | A1 | 8/2003 | Ashton et al. |
| 2004/0019036 | A1 | 1/2004 | Robin et al. |

FOREIGN PATENT DOCUMENTS

| | | |
|---|---|---|
| CS | 269077 | 4/1990 |
| DE | 1922702 | 11/1969 |
| DE | 2105468 | 11/1971 |
| EP | 0286958 A2 | 10/1988 |
| EP | 0334368 A2 | 9/1989 |
| EP | 0393575 B1 | 10/1990 |
| EP | 0515156 B1 | 11/1992 |
| JP | 05219974 | 8/1993 |
| JP | 2002223753 | 8/2002 |
| JP | 2002370939 | 12/2002 |
| JP | 2003310293 | 11/2003 |
| WO | WO 93/01202 | 1/1993 |
| WO | WO 93/07295 | 4/1993 |
| WO | WO 94/26761 | 11/1994 |
| WO | WO 94/27632 | 12/1994 |
| WO | WO 95/15373 | 6/1995 |
| WO | WO 96/11280 | 4/1996 |
| WO | WO 96/36693 | 11/1996 |
| WO | WO 96/39035 | 12/1996 |
| WO | WO 96/40165 | 12/1996 |
| WO | WO 97/23230 | 7/1997 |
| WO | WO 98/16186 | 4/1998 |
| WO | WO 00/23112 | 4/2000 |
| WO | WO 00/40269 | 7/2000 |
| WO | WO 00/62075 | 10/2000 |
| WO | WO 00/74634 A2 | 12/2000 |
| WO | WO 01/29235 A2 | 4/2001 |
| WO | WO 01/69262 A1 | 9/2001 |
| WO | WO 02/21140 A1 | 3/2002 |
| WO | WO 02/053138 A2 | 7/2002 |
| WO | WO 02/057425 A2 | 7/2002 |
| WO | WO 02/069903 A3 | 9/2002 |
| WO | WO 02/076486 A2 | 10/2002 |
| WO | WO 02/083705 A1 | 10/2002 |
| WO | WO 02/085400 A1 | 10/2002 |
| WO | WO 02/087586 A1 | 11/2002 |
| WO | WO 02/101353 A2 | 12/2002 |
| WO | WO 03/012085 A1 | 2/2003 |
| WO | WO 03/012112 A1 | 2/2003 |
| WO | WO 03/020252 A2 | 3/2003 |
| WO | WO 03/026574 A2 | 4/2003 |
| WO | WO 03/031932 | 4/2003 |
| WO | WO 03/040363 A1 | 5/2003 |
| WO | WO 03/043631 A2 | 5/2003 |
| WO | WO 03/046190 A1 | 6/2003 |
| WO | WO 03/062826 A2 | 7/2003 |
| WO | WO 03/065995 A2 | 8/2003 |
| WO | WO 03/076660 A1 | 9/2003 |
| WO | WO 03/092623 A2 | 11/2003 |
| WO | WO 03/104427 A2 | 12/2003 |
| WO | PCT/US04/22367 | 7/2004 |

OTHER PUBLICATIONS

Issa. J.P., Current Opinion in Oncology 15(6): 446-451, 2003.*
Von Hoff, et al., "5-Azacytidine. A New Anticancer Drug With Effectiveness in Acute Myelogenous Leukemia," *Annals of Internal Medicine* (1976) 85(2), pp. 237-245.

(Continued)

*Primary Examiner*—Venkataraman Balasubramanian
(74) *Attorney, Agent, or Firm*—Wilson Sonsini Goodrich & Rosati

(57) ABSTRACT

Compounds and compositions of azacytosine analogs and derivatives are provided. In one aspect of the invention, analogs or derivatives of decitabine and azacitidine are provided with modification at the 4- and 6-position of the triazine ring, at the 1'–6' position of the ribose ring, or combinations thereof. Methods of synthesizing and manufacturing these analogs and derivatives are also provided. These compounds can be formulated into pharmaceutical compositions that can be used for treating any disease that is sensitive to the treatment with decitabine or azacitidine, such as hematological disorders and cancer.

43 Claims, 24 Drawing Sheets

OTHER PUBLICATIONS

Brown, R. et al. Demethylation of DNA by decitabine in cancer chemotherapy. *Expert Rev Anticancer Ther.* 2004; 4(4): 501-510.

Gilbert, J. et al. The Clinical Application of Targeting Cancer through Histone Acetylation and Hypomethylation. *Clinical Cancer Research.* 2004; 10: 4589-4596.

Herman, J. G. et al. Gene Silencing in Cancer in Association with Promoter Hypermethylation. *The New England Journal of Medicine.* 2003; 349(21): 2042-2054.

Leone, G. et al. DNA methylation and demethylating drugs in myelodysplastic syndromes and secondary leukemias. *Haematologica.* 2002; 87(12): 1324-1341.

Leone, G. et al. Inhibitors of DNA methylation in the treatment of hematological malignancies and MDS. *Clin Immunol.* 2003; 109(1): 89-102.

Baylin, S.B. et al. Alterations in DNA Methylation: A Fundamental Aspect of Neoplasia. *Cancer Res.* 1998; 72:141-196.

Daskalakis, M. et al. Expression of a Hypermethylated and Silenced P15/INK4B Gene in a Subgroup of MDS Patients is Restored by Treatment With The Methylation Inhibitor 5-AZA-2'-Deoxycytidine. *Abstracts Leukemia Research.* 2001; Suppl. No. 1:S16-S17.

Esteller, M. A Gene Hypermethylation Profile of Human Cancer. *Cancer Research.* 2001; 61:3225-3229.

Esteller, M. CpG Island Hypermethylation and Tumor Suppressor Genes: a Booming Present, a Brighter Future. *Oncogene.* 2002; 21:5427-5440.

Esteller, M. Epigenetic Lesions Causing Genetic Lesions in Human Cancer: Promoter Hypermethylation of DNA Repair Genes. *European Journal of Cancer.* 2000; 36:2294-2300.

Gagnon, J. et al. Interaction of 5-aza-2'-deoxyctidine and Depsipeptide on Antineoplastic Activity and Activation of 14-3-3σ, E-Cadherin And Tissue Inhibitor of Metalloproteinase 3 Expression in Human Breast Carcinoma Cells. *Anti-Cancer Drugs.* 2003; 14(3):193-202.

Jones, P.A. DNA Methylation And Cancer. *Oncogene,* 2002; 21:5358-5360.

Jones, P.A. et al. The Fundamental Role of Epigenetic Events in Cancer. *Nature Reviews/Genetics.* 2002; 3:415-428.

Jones, P.A. et al. The Role of DNA Methylation in Cancer. *Adv. Cancer Res.* 1990; 54:1-23.

Karpf, A.R. et al. Reactivating The Expression of Methylation Silenced Genes in Human Cancer. *Oncogene.* 2002; 21:5496-5503.

La Rosse, P. et al. *In Vitro* Efficacy of Combined Treatment Depends on the Underlying Mechanism of Resistance in Imatinib-Resistant Bcr-Abl positive Cell Lines. *Blood First Edition Paper.* prepublished online 2003; DOI 10.1182/blood-2003-04-1074, pp. 1-39.

Nephew, K.P. et al. Epigenetic Gene Silencing in Cancer Initiation And Progression. *Cancer Letters.* 2003; 190: 125-133.

Paz, M.F. et al. A Systematic Profile of DNA Methylation in Human Cancer Cell Lines. *Cancer Research.* 2003; 63:1114-1121.

Primeau, M. et al. Synergistic Antineoplastic Action of DNA Methylation Inhibitor 5-AZA-2'-Deoxycytidine and Histone Deacetylase Inhibitor Depsipeptide on Human Breast Carcinoma Cells. *Int. J. Cancer.* 2003; 103:177-184.

Santini, V. et al. Changes in DNA Methylation in Neoplasia: Pathophysiology and Therapeutic Implications. *Annals of Internal Medicine.* 2001; 134:573-586.

Schrump, D.S. et al. Phase 1 Study of Sequential Deoxyazacytidine/Depsipeptide Infusion in Patients With Malignancies Involving Lungs or Pleura. *Clinical Lung Cancer.* 2002; 186-192.

Shaker, S. et al. Preclinical Evaluation of Antineoplastic Activity of Inhibitors of DNA Methylation (5-aza-2'-deoxycytidine) and Histone Deacetylation (Trichostatin A, Depsipeptide) in Combination Against Myeloid Leukemic Cells. *Leukemia Research.* 2003; 27:437-444.

Smiraglia, D.J. et al. The Study of Aberrant Methylation in Cancer *via* Restriction Landmark Genomic Scanning. *Oncogene.* 2002; 21:5414-5426.

Wajed, S.A. et al. DNA Methylation: An Alternative Pathway to Cancer. *Annals of Surgery* 2001; 234(1):10-20.

Weiser, T.S. Sequential 5-Aza-2'-Deoxycytidine-Depsipeptide FR901228 Treatment Induces Apoptosis Preferentially in Cancer Cells And Facilities Their Recognition by Cytolytic T Lymphocytes Specific for NY-ESO-1. *Journal of Immunotherapy.* 2001; 24(2):151-161.

\* cited by examiner

Decitabine (1a)          Azacitidine (1b).

Cytarabine (1c)    6-Azacytidine (1d).

1'i $R_z$ = OMe, R = ClBz
1'a $R_z$ = OMe, R = H
1'b $R_z$ = N(CH$_3$)$_2$, R = H
1'c $R_z$ = NHNH$_2$, R = H
1'd $R_z$ = NHCH$_3$, R = H
1'e $R_z$ = NHC$_2$H$_5$, R = H
1'f $R_z$ = NHC$_3$H$_7$, R = H
1'g $R_z$ = NHC$_6$H$_5$, R = H

1"j $R_z$ = OMe, R = ClBz
1"a $R_z$ = OMe, R = H
1"b $R_z$ = N(CH$_3$)$_2$, R = H
1"c $R_z$ = NHNH$_2$, R = H
1"d $R_z$ = NHCH$_3$, R = H
1"e $R_z$ = NHC$_2$H$_5$, R = H
1"f $R_z$ = NHC$_3$H$_7$, R = H
1"g $R_z$ = NHC$_6$H$_5$, R = H

12 R = H
13 R = OH

89

90

91

92

93

94

95

96

97

98

99

100

101

102

103

AZACYTOSINE ANALOGS AND DERIVATIVES

BACKGROUND OF THE INVENTION

1. Field of the Invention

The present invention relates to compounds and compositions of cytosine analogs and derivatives, and methods for preparing, formulating and administering these compounds or compositions to a host in need thereof.

2. Description of Related Art

A few nucleosides of azacytosine, such as 5-aza-2'-deoxycytidine (also called decitabine, FIG. 1A, structure 1a) and azacitidine (FIG. 1A, structure 1b), have been developed as antagonist of its related natural nucleoside, cytidine and 2'-deoxycytidine, respectively. The only structural difference between azacytosine and cytosine is the presence of a nitrogen atom at position 5 of the cytosine ring in azacytosine as compared to a carbon at this position for cytosine. Decitabine (1a) was prepared by cyclization of peracylglycosyl isocyanates (Pliml and Sorm (1964) Collect. Czech. Chem. Commun. 29:2576–2577); later azacitidine (1b) and a series of related analogues were prepared (Naeem et. al. (1998) Collect. Czech. Chem. Commun. 63:222–230).

Two isomeric forms of decitabine can be distinguished. The β-anomer is the active form. The modes of decomposition of decitabine in aqueous solution are (a) conversion of the active β-anomer to the inactive α-anomer (Pompon et al. (1987) J. Chromat. 388:113–122); (b) ring cleavage of the aza-pyrimidine ring to form N-(formylamidino)-N'-β-D-2'-deoxy-(ribofuranosy)-urea (Mojaverian and Repta (1984) J. Pharm. Pharmacol. 36:728–733); and (c) subsequent forming of guanidine compounds (Kissinger and Stemm (1986) J. Chromat. 353:309–318).

Decitabine possesses multiple pharmacological characteristics. At a molecular level, it is S-phase dependent for incorporation into DNA. At a cellular level, decitabine can induce cell differentiation and exert hematological toxicity. Despite having a short half life in vivo, decitabine has an excellent tissue distribution.

One of the function of decitabine is its ability to specifically and potently inhibit DNA methylation. Methylation of cytosine to 5-methylcytosine occurs at the level of DNA. Inside the cell, decitabine is first converted into its active form, the phosphorylated 5-aza-deoxycytidine, by deoxycytidine kinase which is primarily synthesized during the S phase of the cell cycle. The affinity of decitabine for the catalytical site of deoxycytidine kinase is similar to the natural substrate, deoxycytidine.

Momparler et al. (1985) 30:287–299. After conversion to its triphosphate form by deoxycytidine kinase, decitabine is incorporated into replicating DNA at a rate similar to that of the natural substrate, dCTP. Bouchard and Momparler (1983) Mol. Pharmacol. 24:109–114.

Incorporation of decitabine into the DNA strand has a hypomethylation effect. Each class of differentiated cells has its own distinct methylation pattern. After chromosomal duplication, in order to conserve this pattern of methylation, the 5-methylcytosine on the parental strand serves to direct methylation on the complementary daughter DNA strand. Substituting the carbon at the 5 position of the cytosine for a nitrogen interferes with this normal process of DNA methylation. The replacement of 5-methylcytosine with decitabine at a specific site of methylation produces an irreversible inactivation of DNA methyltransferase, presumably due to formation of a covalent bond between the enzyme and decitabine. Juttermann et al. (1994) Proc. Natl. Acad. Sci. USA 91:11797–11801. By specifically inhibiting DNA methyltransferase, the enzyme required for methylation, the aberrant methylation of the tumor suppressor genes can be prevented.

Decitabine is commonly supplied as a sterile lyophilized powder for injection, together with buffering salt, such as potassium dihydrogen phosphate, and pH modifier, such as sodium hydroxide. For example, decitabine is supplied by SuperGen, Inc., as lyophilized powder packed in 20 mL glass vials, containing 50 mg of decitabine, monobasic potassium dihydrogen phosphate, and sodium hydroxide. When reconstituted with 10 mL of sterile water for injection, each mL contain 5 mg of decitabine, 6.8 mg of $KH_2PO_4$, and approximately 1.1 mg NaOH. The pH of the resulting solution is 6.5–7.5. The reconstituted solution can be further diluted to a concentration of 1.0 or 0.1 mg/mL in cold infusion fluids, i.e., 0.9% Sodium Chloride; or 5% Dextrose; or 5% Glucose; or Lactated Ringer's. The unopened vials are typically stored under refrigeration (2–8° C.; 36–46° F.), in the original package.

Decitabine is most typically administrated to patients by injection, such as by a bolus I.V. injection, continuous I.V. infusion, or I.V. infusion. The length of I.V. infusion is limited by the decomposition of decitabine in aqueous solutions.

Thus, a need still exists for compounds, compositions and methods for improving chemical stability of cytosine analogs, especially in aqueous solutions. The present invention provides such improvements.

SUMMARY OF THE INVENTION

Compounds, salts and compositions of cytosine analogs and derivatives are provided. In one aspect of the invention, analogs or derivatives of decitabine and azacitidine are provided with modification at the 4- and 6-position of the triazine ring, at the 1'–6'position of the ribose ring, or combinations thereof.

In one embodiment, a compound of Formula I is provided.

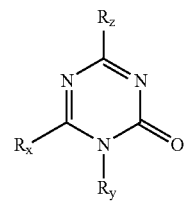

In a variant of the embodiment, group $R_x$ of Formula I is a halogen (i.e., fluoride, chloride, bromide, or iodide), and preferably fluoride.

According to the embodiment, group $R_y$ of Formula I is preferably a hydrogen, alkyl, aryl, or sugar, and more preferably a substituted or unsubstituted ribofuranose or 2'-deoxyribofuranose.

According to the embodiment, group $R_z$ of Formula I is preferably a hydrogen, amino, alkyl, aryl, arylalkyl, alkylamino, dialkylamino, alkylarylamino, hydrazine, or hydroxylalkylamino.

In another variant of the embodiment, group $R_x$ of Formula I is preferably a strong electron-donating group such as hydroxyl, thiol, primary, secondary or tertiary amino, —O-alkyl, —S-alkyl, —O-aryl and —S-aryl. Strong electron-donating group is defined as the class of chemical moieties that can decrease the electrophilicity of an adjacent site by resonance or inductive effects.

In yet another variant of the embodiment, group $R_x$ of Formula I is hydrogen, alkyl (preferably straight or branched chain $C_{1-6}$ alkyl), aryl, halogen-substituted alkyl or aryl (preferably mono-, di- or trifluoromethyl), phenyl, or benzyl, provided that when $R_x$ is hydrogen, methyl, chloromethyl, phenyl or benzyl, and $R_y$ is hydrogen or glycosyl, $R_z$ is not amino or dimethyl amino.

In another embodiment, a compound of Formula II is provided.

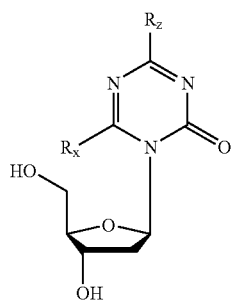

II

In a variant of the embodiment, group $R_x$ of Formula II is a halogen (i.e., fluoride, chloride, bromide, or iodide), and preferably fluoride.

In another variant of the embodiment, group $R_x$ of Formula II is preferably a strong electron-donating group such as hydroxyl, thiol, primary, secondary or tertiary amino, —O-alkyl, —S-alkyl, —O-aryl and —S-aryl.

According to the embodiment, group $R_z$ of Formula I is preferably a hydrogen, amino, alkyl, aryl, arylalkyl, alkylamino, dialkylamino, alkylarylamino, hydrazine, and hydroxylalkylamino.

In yet another variant of the embodiment, group $R_x$ of Formula I is hydrogen, alkyl (preferably straight or branched chain $C_{1-6}$ alkyl), aryl, halogen-substituted alkyl or aryl (preferably mono-, di- or trifluoromethyl), phenyl, or benzyl, provided that when $R_x$ is hydrogen, methyl, chloromethyl, phenyl or benzyl, $R_z$ is not amino or dimethyl amino.

In yet another embodiment, a compound of Formula III is provided.

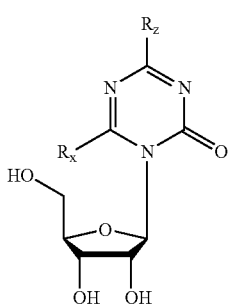

III

In a variant of the embodiment, group $R_x$ of Formula III is a halogen (i.e., fluoride, chloride, bromide, or iodide), and preferably fluoride.

In another variant of the embodiment, group $R_x$ of Formula III is preferably a strong electron-donating group such as hydroxyl, thiol, amino, —N-alkyl, —O-alkyl, —S-alkyl, —N-aryl, —O-aryl and —S-aryl.

According to the embodiment, group $R_z$ of Formula I is preferably a hydrogen, amino, alkyl, aryl, arylalkyl, alkylamino, dialkylamino, alkylarylamino, hydrazine, and hydroxylalkylamino.

In yet another variant of the embodiment, group $R_x$ of Formula I is hydrogen, alkyl (preferably straight or branched chain $C_{1-6}$ alkyl), aryl, halogen-substituted alkyl or aryl (preferably mono-, di- or trifluoromethyl), phenyl, or benzyl, provided that when $R_x$ is hydrogen, methyl, chloromethyl, phenyl or benzyl, $R_z$ is not amino or dimethyl amino.

In yet another embodiment, a compound of Formula IV is provided.

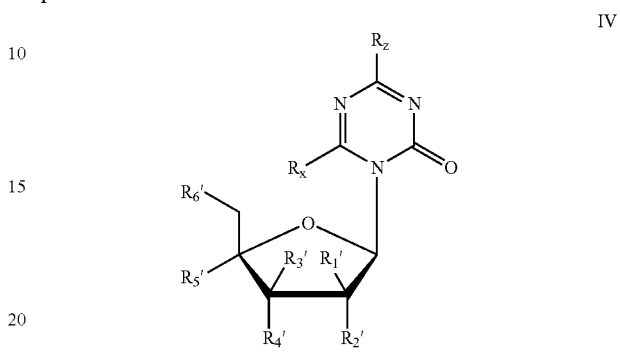

IV

In a variant of the embodiment, group $R_x$ of Formula IV is hydrogen, alkyl (preferably straight or branched chain $C_{1-6}$ alkyl), aryl, halogen-substituted alkyl or aryl (preferably mono-, di- or trifluoromethyl), phenyl, or benzyl.

In another variant of the embodiment, group $R_x$ of Formula IV is a halogen (i.e., fluoride, chloride, bromide, or iodide), and preferably fluoride.

In yet another variant of the embodiment, group $R_x$ of Formula IV is preferably an electron-donating group, and more preferably a strong electron-donating group such as hydroxyl, thiol, amino, —N-alkyl, —O-alkyl, —S-alkyl, —N-aryl, —O-aryl and —S-aryl.

According to the embodiment, group $R_z$ of Formula I is preferably a hydrogen, amino, alkyl, aryl, arylalkyl, alkylamino, dialkylamino, alkylarylamino, hydrazine, and hydroxylalkylamino.

According to the embodiment, group $R_1'$, $R_2'$, $R_3'$, $R_4'$, $R_5'$, or $R_6'$ of Formula IV is each independently selected from the group consisting of hydrogen, hydroxyl, fluoride, choloride, bromide, iodide, $CF_3$, —O-alkyl, —O-acyl, —O-aryl, —S-alkyl, and —S-aryl, provided that when $R_x$ is hydrogen and $R_z$ is amino, $R_4'$ is not hydroxyl. Preferably, $R_4'$ is hydrogen and $R_1'$, $R_2'$, $R_3'$, $R_5'$, or $R_6'$ is independently hydrogen, fluoride, chloride, bromide, iodide, $CF_3$, —O-alkyl, —O-acyl, —O-aryl, —S-alkyl, or —S-aryl.

The invention also provides a salt form of azacytosine analogs and derivatives, more preferably pharmaceutically-acceptable salts of the compounds of the invention (preferably a compound of Formulas I–IV).

In one embodiment, salt of a compound of Formula I is provided,

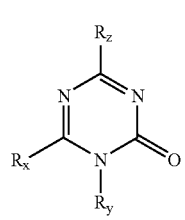

I wherein $R_x$ is hydrogen, alkyl, aryl, halogen-substituted alkyl or aryl, phenyl, or benzyl; $R_y$ is hydrogen, alkyl, or sugar; and $R_z$ is a hydrogen, amino, alkyl, aryl, arylalkyl, alkylamino, dialkylamino, alkylarylamino, hydrazine, or hydroxylalkylamino, provided that when $R_y$ is 2'-deoxy-D-ribose or D-ribose, $R_x$ is not hydrogen and $R_z$ is not amino.

According to the embodiment, the salt may be synthesized with an acid such as hydrochloric, L-lactic, acetic, phosphoric, (+)-L-tartaric, citric, propionic, butyric, hexanoic, L-aspartic, L-glutamic, succinic, EDTA, maleic, and methanesulfonic acid; HBr, HF, HI, nitric, nitrous, sulfuric, sulfurous, phosphorous, perchloric, chloric, and chlorous acid; carboxylic acid such as ascorbic, carbonic, and fumaric acid; sulfonic acid such as ethanesulfonic, 2-hydroxyethanesulfonic, and toluenesulfonic acid;.

Also according to the embodiment, the salt is preferably a hydrochloride, mesylate, EDTA, sulfite, L-Aspartate, maleate, phosphate, L-Glutamate, (+)-L-Tartrate, citrate, L-Lactate, succinate, acetate, hexanoate, butyrate, or propionate salt.

Methods of synthesizing and manufacturing these analogs and derivatives are also provided. These compounds can be formulated into pharmaceutical compositions that can be used for treating any disease that is sensitive to the treatment with decitabine or azacitidine, such as hematological disorders and cancer.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention provides novel azacytosine analogs and derivatives, pharmaceutically acceptable salts and composition thereof. The invention circumvents limitations of DNA methylation inhibitors such as decitabine and azacitidine, including fast decomposition in aqueous solutions and discomfort to patients due to cold infusions of decitabine and azacitidine. Leveraging their knowledge based on analysis of studies conducted on hydrolysis of decitabine and azacitidine under various conditions and analysis of resonance of the triazine ring of these two compounds, the inventors provide solutions to the instability problems of azacytidine compounds through modification of the triazine ring and the ribose ring. Compared to the unmodified azacytidines, the inventive compounds and compositions should have superior long-term chemical stability, convenient storage and administration, and cause less discomfort to patients due to cold infusions.

The compounds and compositions of present invention can be used to treat patient suffering from a disease sensitive to the treatment with decitabine or azacitidine, such as hematological disorders, benign tumors, malignant tumors, restenosis, and inflammatory diseases via various routes of administration such as intravenous, intramuscular, subcutaneous injection, oral administration and inhalation.

The present invention also provides methods for designing chemically stable azacytosine analogs, methods of synthesizing, formulating and manufacturing these compounds and compositions thereof.

The following is a detailed description of the invention and preferred embodiments of the inventive compounds, compositions, methods of use, synthesis, formulation and manufacture.

Figure 1:
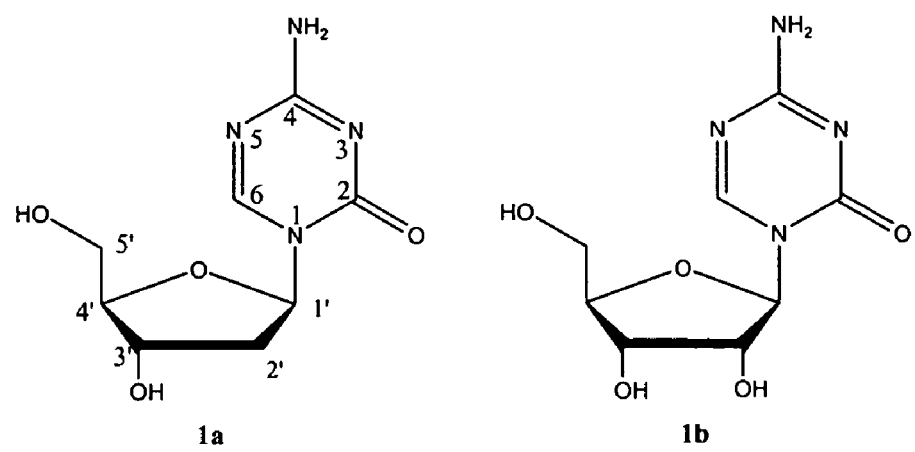
FIG. 1 illustrates chemical structures of decitabine and azacitidine.
Figure 2:
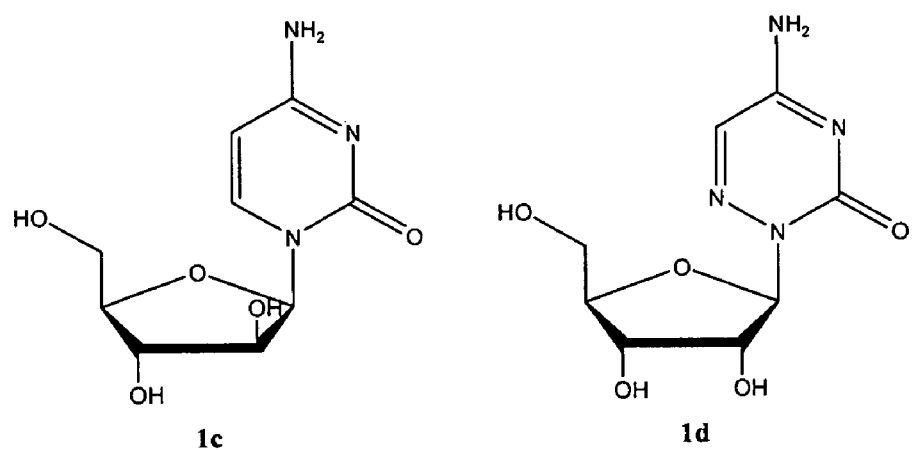
FIG. 2 illustrates chemical structures of cytarabine and 6-azacytidine.
Figure 3A:
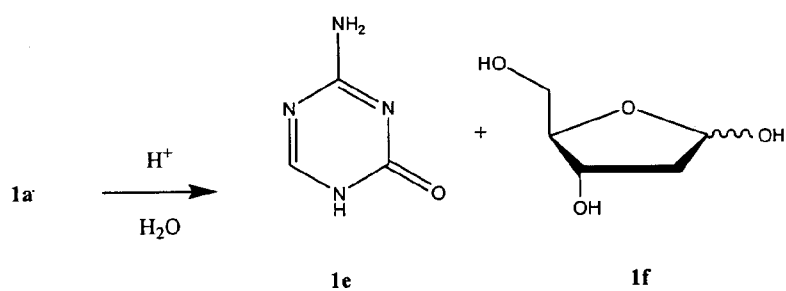
FIG. 3A is a scheme of hydrolysis of decitabine in acidic medium.
Figure 3B:
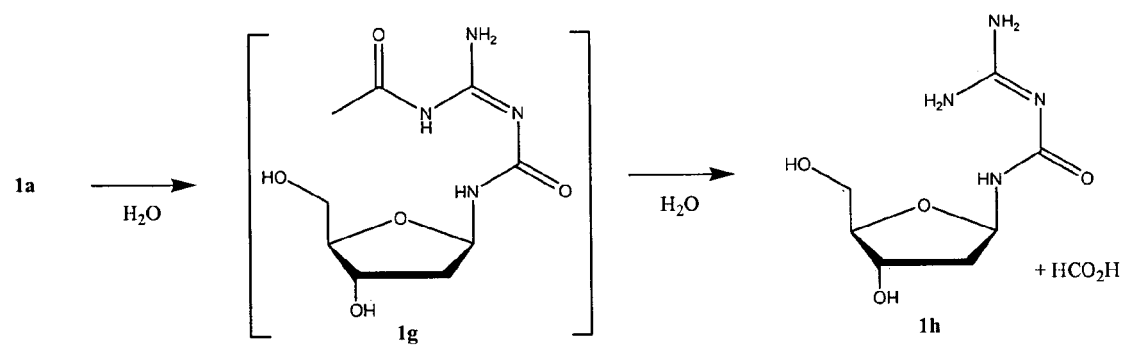
FIG. 3B is a scheme of hydrolysis of decitabine in neutral medium.

1. Problems of Chemical and Physiological Instability of Decitabine and Azacitidine and Solutions Provided by the Invention Decitabine and azacitidine are unstable in aqueous media and undergo hydrolytic degradation. In acidic medium, decitabine is hydrolyzed at room temperature to 5-azacytosine (1e) and 2-deoxyribose (1f, FIG. 3A). In neutral medium at room temperature, the opening of the triazine ring takes place at the 6-position to form the transient intermediate formyl derivative (1g), which is further hydrolyzed to the amidino-urea derivative (1h) and formic acid (FIG. 3B) (Piskala, A.; Synackova, M.; Tomankova, H.; Fiedler, P.; Zizkowsky, V. *Nucleic Acids Res.* 1978, 4, s109-s-113.). This hydrolysis at the 6-position also occurs in acidic and basic aqueous media at even faster rates.

Figure 3C:
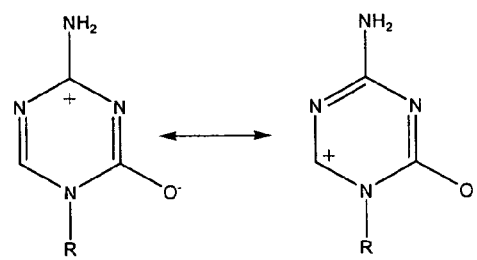
FIG. 3C is a schematic illustration of resonance of the triazine ring of decitabine and azacitidine.

The inventors believe that the hydrolysis is due to the fact that the 6-position is very electrophilic and open to nucleophilic attack by a water molecule, which leads to hydrolytic cleavage. Based on this theory, resonance analysis of the triazine ring was conducted to show that the 6-position is both electrophilic and less sterically hindered than the next electrophilic site (FIG. 3C): the 6-position carbocation (secondary carbon) is bonded with only two nitrogen atoms, while the 4-position carbocation tertiary carbon) is bonded with three nitrogen atoms. This supports the inventor's belief and explains why the 6-position of the triazine ring is liable to undergo hydrolytic cleavage.

As described above, in aqueous media of varying pH, decitabine undergoes rapid hydrolytic cleavages. In alkaline medium the hydrolysis to the amidino-urea derivative (1h) occurs even faster, within a few minutes. Azacitidine also undergoes similar degradation in aqueous media at all pHs.

Decitabine and azacitidine are also unstable in biological fluid due to deamination. The deamination of decitabine to 5-aza-2'-deoxyuridine is catalyzed by cytidine deaminase. Chabot et al. (1983) Biochemical Pharmacology 22:1327–1328. The estimated $K_m$ of decitabine was 250 µM for the enzyme purified from human liver as compared to the $K_m$ of 12 µM for the natural substrate, deoxycytidine. The rate of deamination of deoxycytidine was about 6-fold greater than that of decitabine by cytidine deaminase at equal concentrations.

Figure 3D:
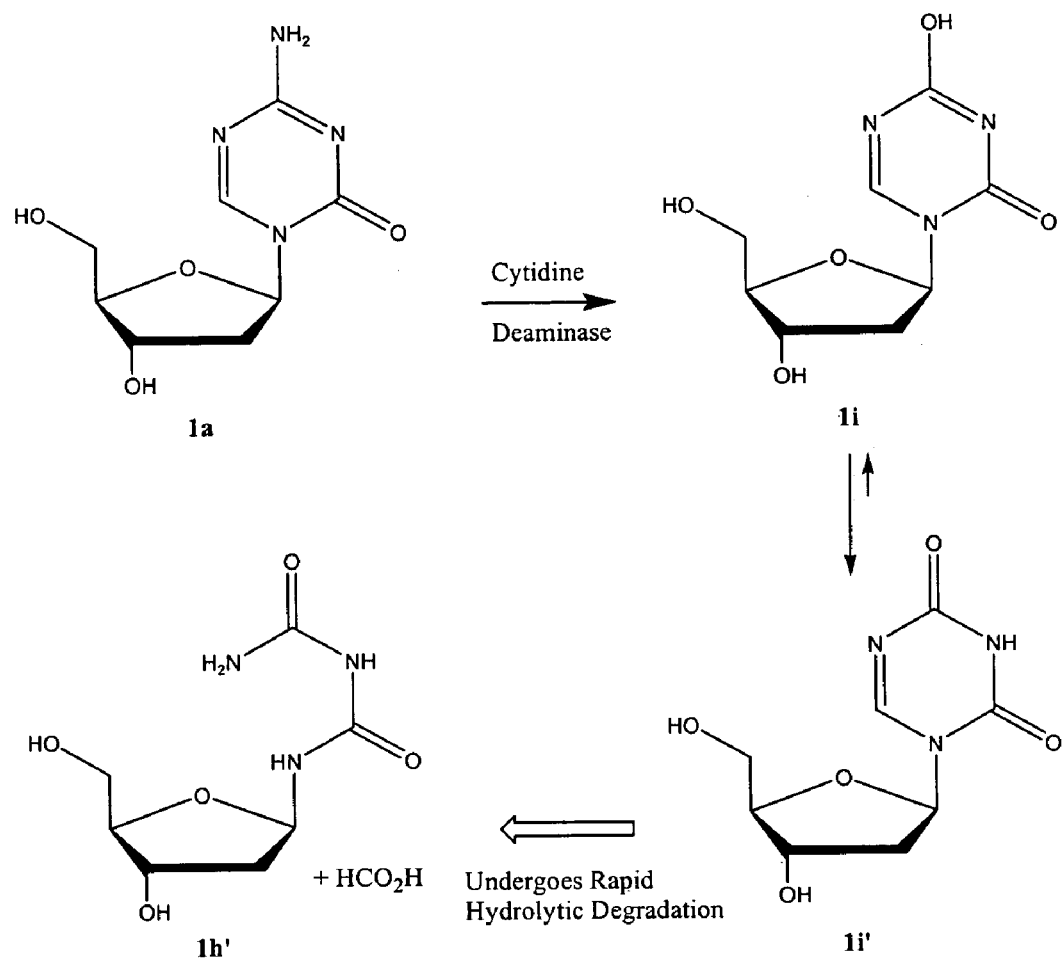
FIG. 3D is a scheme of deamination of decitabine by cytidine deaminase.

The enol derivative after deamination (1i, FIG. 3D) should have retained its capacity to bind and inhibit methyltransferase; however, the more thermodynamically favorable keto tautomer (1i') has a carbonyl functional group at the 4-position, which makes the 6-position highly electrophilic and undergoes hydrolytic cleavage. Thus, a possible mechanism of resistance to decitabine is an increase in the levels of the deaminating enzyme cytidine deaminase. Treatment with decitabine has been associated with an increase in the cytidine deaminase activity in HL-60 cells and in leukemic cells in some patients. To increase the stability of cytosine nucleotides such as decitabine and azacitidine, the inventors believe that this susceptibility toward deamination and predisposition toward hydrolytic cleavage of the triazine ring before and after deamination of the 4-position NH2 group by cytidine deaminase should be removed by modifying the ring in various ways as provided below (examples shown in FIGS. 4B, C, D; 6B, C; 8D, E, F, G). When the 4-position is substituted by stronger bases (1'b–1'g, 1'''b–1'''g, FIG. 4D) or substituted by an equivalent electron-donating group that does not tautomerize (1'a, 1''a, 2a, 3a, 4a, 5a, 6a, 7a, 8a, 9a, 10a, 11a, FIGS. 4B, C, D), the potential for deamination and subsequent hydrolytic cleavage is minimized. When the 6-position is substituted electron-donating groups (FIGS. 4B, C; 6B, C; 8A, B), the propensity toward hydrolytic cleavage is also minimized.

The inventors believe that the inventive compounds represent a new generation of hypomethylating agents that not only retain the unique mechanism of action of decitabine and azacitidine but also have improved aqueous stability and activity. Increased stability of the inventive compounds should make manufacturing of the active pharmaceutical ingredient (API) and drug product more robust and economical, facilitate development of different, more patient-friendly formulations, and increase bioavailability of the drug.

Preferred embodiments of the inventive compounds are described in detail in the following section.

2. Azacytosine Analogs and Derivatives According to the Invention

The present invention provides azacytosine analogs and derivatives with improved chemical stability in aqueous solution and against cytidine deaminase. Preferred embodiments are shown as chemical formula or described in the text of the specification.

As used herein, the term "alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

In addition, the term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, and most preferably from 1–5 carbon atoms.

As used herein, the term "alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

As used herein, the term "alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

As used herein, the term "alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

As used herein, the term "acyl" refers to a group —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cylcohexylcarbonyl, cyclohexylmethylcarbonyl, benzoyl, benzylcarbonyl and the like.

As used herein, the term "acylamino" (or alternatively "acylamido") refers to a group —NR'C(O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino (i.e., acetamido), cyclohexylcarbonylamino, cyclohexylmethylcarbonylamino, benzoylamino (i.e., benzamido), benzylcarbonylamino and the like.

As used herein, the term "acyloxy" refers to a group —OC(O)R, where R is hydrogen, alkyl, cycloalkyl, cycloheteroalkyl, aryl, arylalkyl, heteroalkyl, heteroaryl or heteroarylalkyl, as defined herein. Representative examples include, but are not limited to, acetyloxy (or acetoxy), butyloxy (or butoxy), benzoyloxy and the like.

As used herein, the term "alkylamino" means a group —NHR where R represents an alkyl or cycloalkyl group as defined herein. Representative examples include, but are not limited to, methylamino, ethylamino, 1-methylethylamino, cyclohexyl amino and the like.

As used herein, the term "alkoxy" refers to a group —OR where R represents an alkyl or cycloalkyl group as defined herein. Representative examples include, but are not limited to, methoxy, ethoxy, propoxy, butoxy, cyclohexyloxy and the like.

As used herein, the term "alkoxycarbonyl" refers to a group —C(O)-alkoxy where alkoxy is as defined herein.

As used herein, the term "alkylsulfonyl" refers to a group —S(O)$_2$R where R is an alkyl or cycloalkyl group as defined herein. Representative examples include, but are not limited to, methylsulfonyl, ethylsulfonyl, propylsulfonyl, butylsulfonyl and the like.

As used herein, the term "alkylsulfinyl" refers to a group —S(O)R where R is an alkyl or cycloalkyl group as defined herein. Representative examples include, but are not limited to, methylsulfinyl, ethylsulfinyl, propylsulfinyl, butylsulfinyl and the like.

As used herein, the term "alkylthio" refers to a group —SR where R is an alkyl or cycloalkyl group as defined herein that may be optionally substituted as defined herein. Representative examples include, but are not limited to methylthio, ethylthio, propylthio, butylthio and the like.

As used herein, the term "amino" refers to the group —NH$_2$.

As used herein, the term "aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably between 6 to 12 carbon atoms.

As used herein, the term "arylalkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$) and the aryl moiety is ($C_6$–$C_{20}$), more preferably, an arylalkyl group is ($C_6$–$C_{20}$) arylalkyl, e.g., the alkanyl, alkenyl or alkynyl moiety of the arylalkyl group is ($C_1$–$C_8$) and the aryl moiety is ($C_6$–$C_{12}$).

As used herein, the term "arylalkyloxy" refers to an —O-arylalkyl group where arylalkyl is as defined herein.

As used herein, the term "aryloxycarbonyl" refers to a group —C(O)—O-aryl where aryl is as defined herein.

As used herein, the terms "hydroxylalkylamino" and "hydroxylarylamino" refer to a group —NHROH where R represents an alkyl or aryl substituted with a hydroxyl —OH group.

As used herein, the terms "thiolalkylamino" and "thiolarylamino" refer to a group —NHRSH where R represents an alkyl or aryl substituted with a thiol —SH group.

In one embodiment, a compound of Formula I is provided.

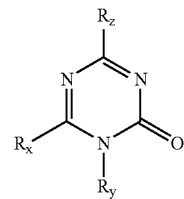

I

In a variant of the embodiment, group $R_x$ of Formula I is a halogen (i.e., fluoride, chloride, bromide, or iodide), and preferably fluoride.

According to the embodiment, group $R_y$ of Formula I is preferably a hydrogen, alkyl, aryl, or sugar, and more preferably a substituted or unsubstituted ribofuranose or 2'-deoxyribofuranose.

According to the embodiment, group $R_z$ of Formula I is preferably a hydrogen, amino, alkyl, aryl, arylalkyl, alkylamino, dialkylamino, alkylarylamino, hydrazine, or hydroxylalkylamino.

In another variant of the embodiment, group $R_x$ of Formula I is preferably a strong electron-donating group such as hydroxyl, thiol, primary, secondary or tertiary amino, —O-alkyl, —S-alkyl, —O-aryl and —S-aryl. Strong electron-donating group is defined as the class of chemical moieties that can decrease the electrophilicity of an adjacent site by resonance or inductive effects.

In yet another variant of the embodiment, group $R_x$ of Formula I is hydrogen, alkyl (preferably straight or branched chain $C_{1-6}$ alkyl), aryl, halogen-substituted alkyl or aryl (preferably mono-, di- or trifluoromethyl), phenyl, or benzyl, provided that when $R_x$ is hydrogen, methyl, chloromethyl, phenyl or benzyl, and $R_y$ is hydrogen or glycosyl, $R_z$ is not amino or dimethyl amino.

In another embodiment, a compound of Formula II is provided.

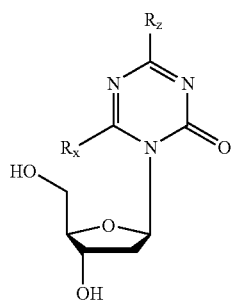

II

In a variant of the embodiment, group $R_x$ of Formula II is a halogen (i.e., fluoride, chloride, bromide, or iodide), and preferably fluoride.

In another variant of the embodiment, group $R_x$ of Formula II is preferably a strong electron-donating group such as hydroxyl, thiol, primary, secondary or tertiary amino, —O-alkyl, —S-alkyl, —O-aryl and —S-aryl.

According to the embodiment, group $R_z$ of Formula I is preferably a hydrogen, amino, alkyl, aryl, arylalkyl, alkylamino, dialkylamino, alkylarylamino, hydrazine, and hydroxylalkylamino.

In yet another variant of the embodiment, group $R_x$ of Formula I is hydrogen, alkyl (preferably straight or branched chain $C_{1-6}$ alkyl), aryl, halogen-substituted alkyl or aryl (preferably mono-, di- or trifluoromethyl), phenyl, or benzyl, provided that when $R_x$ is hydrogen, methyl, chloromethyl, phenyl or benzyl, $R_z$ is not amino or dimethyl amino.

In yet another embodiment, a compound of Formula III is provided.

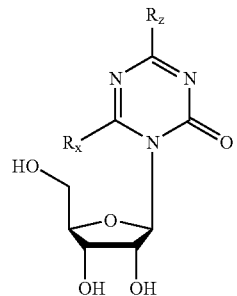

III

In a variant of the embodiment, group $R_x$ of Formula III is a halogen (i.e., fluoride, chloride, bromide, or iodide), and preferably fluoride.

In another variant of the embodiment, group $R_x$ of Formula III is preferably a strong electron-donating group such as hydroxyl, thiol, amino, —N-alkyl, —O-alkyl, —S-alkyl, —N-aryl, —O-aryl and —S-aryl.

According to the embodiment, group $R_z$ of Formula I is preferably a hydrogen, amino, alkyl, aryl, arylalkyl, alkylamino, dialkylamino, alkylarylamino, hydrazine, and hydroxylalkylamino.

In yet another variant of the embodiment, group $R_x$ of Formula I is hydrogen, alkyl (preferably straight or branched chain $C_{1-6}$ alkyl), aryl, halogen-substituted alkyl or aryl (preferably mono-, di- or trifluoromethyl), phenyl, or benzyl, provided that when $R_x$ is hydrogen, methyl, chloromethyl, phenyl or benzyl, $R_z$ is not amino or dimethyl amino.

In yet another embodiment, a compound of Formula IV is provided.

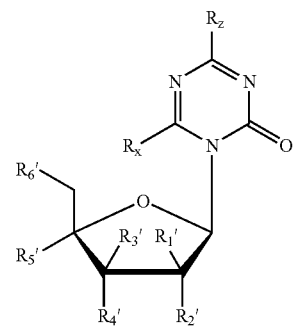

IV

In a variant of the embodiment, group $R_x$ of Formula IV is hydrogen, alkyl (preferably straight or branched chain $C_{1-6}$ alkyl), aryl, halogen-substituted alkyl or aryl (preferably mono-, di- or trifluoromethyl), phenyl, or benzyl.

In another variant of the embodiment, group $R_x$ of Formula IV is a halogen (i.e., fluoride, chloride, bromide, or iodide), and preferably fluoride.

In yet another variant of the embodiment, group $R_x$ of Formula IV is preferably an electron-donating group, and more preferably a strong electron-donating group such as hydroxyl, thiol, amino, —N-alkyl, —O-alkyl, —S-alkyl, —N-aryl, —O-aryl and —S-aryl.

According to the embodiment, group $R_z$ of Formula I is preferably a hydrogen, amino, alkyl, aryl, arylalkyl, alkylamino, dialkylamino, alkylarylamino, hydrazine, and hydroxylalkylamino.

According to the embodiment, group $R_1'$, $R_2'$, $R_3'$, $R_4'$, $R_5'$, or $R_6'$ of Formula IV is each independently selected from the group consisting of hydrogen, hydroxyl, fluoride, choloride, bromide, iodide, $CF_3$, —O-alkyl, —O-acyl, —O-aryl, —S-alkyl, and —S-aryl, provided that when $R_x$ is hydrogen and $R_z$ is amino, $R_4'$ is not hydroxyl. Preferably, $R_4'$ is hydrogen and $R_1'$, $R_2'$, $R_3'$, $R_5'$, or $R_6'$ is independently hydrogen, fluoride, chloride, bromide, iodide, $CF_3$, —O-alkyl, —O-acyl, —O-aryl, —S-alkyl, or —S-aryl.

The compounds of the invention (preferably compounds of Formulas I–IV) can possess one or more asymmetric carbon atoms and are thus capable of existing in the form of optical isomers as well as in the form of racemic or non-racemic mixtures thereof. The compounds of the invention (preferably compounds of Formulas I–IV) can be utilized in the present invention as a single isomer or as a mixture of stereochemical isomeric forms.

Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts.

An alternative process for separation of optical isomers includes the use of a chiral chromatography column optimally chosen to maximize the separation of the enantiomers. Still another available method involves synthesis of covalent diastereoisomeric molecules by reacting compounds of the invention (preferably compounds of Formula I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention (preferably compounds of Formulas I–IV) can likewise be obtained by utilizing optically active starting materials. These isomers may be in the form of a free acid, a free base, an ester or a salt.

The invention also embraces pharmaceutically-acceptable salts of the compounds of the invention (preferably a compound of Formulas I–IV).

In one embodiment, salt of a compound of Formula I is provided,

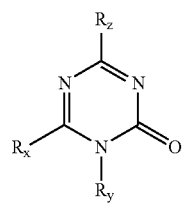

I wherein $R_x$ is hydrogen, alkyl, aryl, halogen-substituted alkyl or aryl, phenyl, or benzyl; $R_y$ is hydrogen, alkyl, or sugar; and $R_z$ is a hydrogen, amino, alkyl, aryl, arylalkyl, alkylamino, dialkylamino, alkylarylamino, hydrazine, or hydroxylalkylamino, provided that when $R_y$ is 2'-deoxy-D-ribose or D-ribose, $R_x$ is not hydrogen and $R_z$ is not amino.

The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of the invention (preferably a compound of Formulas I–IV) may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, .beta.-hydroxybutyric, malonic, galactic, and galacturonic acid. Suitable pharmaceutically-acceptable base addition salts of compounds of the invention (preferably a compound of Formulas I–IV) include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine and procaine. All of these salts may be prepared by conventional means from the corresponding compound of the invention (preferably a compound of Formulas I–IV) by treating, for example, the compound of the invention (preferably a compound of Formulas I–IV) with the appropriate acid or base.

The invention also embraces isolated compounds. An isolated compound refers to a compound which represents at least 10%, preferably 20%, more preferably 50% and most preferably 80% of the compound present in the mixture, and exhibits a detectable (i.e. statistically significant) inhibitory activity of DNA methylation when tested in biological assays such as the combined bisulfite restriction analysis or COBRA (Xiong, Z.; Laird, P. W. *Nucleic Acids Res.* 1997, 25, 2532–2534) and radiolabeled methyl incorporation assay (Francis, K. T.; Thompson, R. W.; Krumdieck, C. L. *Am. J. Clin. Nutr.* 1977, 30, 2028–2032)

3. Pharmaceutical Formulations of the Present Invention

According to the present invention, the cytosine analogs and derivatives can be formulated into pharmaceutically acceptable compositions for treating various diseases and conditions.

The pharmaceutically-acceptable compositions of the present invention comprise one or more compounds of the invention (preferably compounds of Formula I–IV) in association with one or more nontoxic, pharmaceutically-acceptable carriers and/or diluents and/or adjuvants and/or excipients, collectively referred to herein as "carrier" materials, and if desired other active ingredients.

The compounds of the present invention (preferably compounds of Formula I–IV) are administered by any route, preferably in the form of a pharmaceutical composition adapted to such a route, as illustrated below and are dependent on the condition being treated. The compounds and compositions can be, for example, administered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by a catheter or stent), subcutaneously, intraadiposally, intraarticularly, or intrathecally.

The pharmaceutical formulation may optionally further include an excipient added in an amount sufficient to enhance the stability of the composition, maintain the product in solution, or prevent side effects (e.g., potential ulceration, vascular irritation or extravasation) associated with the administration of the inventive formulation. Examples of excipients include, but are not limited to, mannitol, sorbitol, lactose, dextrox, cyclodextrin such as, α-, β-, and γ-cyclodextrin, and modified, amorphous cyclodextrin such as hydroxypropyl-, hydroxyethyl-, glucosyl-, maltosyl-, maltotriosyl-, carboxyamidomethyl-, carboxymethyl-, sulfobutylether-, and diethylamino-substituted α-, β-, and γ-cyclodextrin. Cyclodextrins such as Encapsin® from Janssen Pharmaceuticals or equivalent may be used for this purpose.

For oral administration, the pharmaceutical compositions can be in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maizestarch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery.

The pharmaceutical compositions can be administered via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

In a particular embodiment, the compound of the present invention can be formulated into a pharmaceutically acceptable composition comprising the compound solvated in non-aqueous solvent that includes glycerin, propylene glycol, polyethylene glycol, or combinations thereof. It is believed that the compound decitabine will be stable in such pharmaceutical formulations so that the pharmaceutical formulations may be stored for a prolonged period of time prior to use.

As discussed above, in current clinical treatment with decitabine, to minimize drug decomposition decitabine is supplied as lyophilized powder and reconstituted in a cold aqueous solution containing water in at least 40% vol of the solvent, such as WFI, and diluted in cold infusion fluids prior to administration. Such a formulation and treatment regimen suffers from a few drawbacks. First, refrigeration of decitabine in cold solution becomes essential, which is burdensome in handling and economically less desirable than a formulation that can sustain storage at higher temperatures. Second, due to rapid decomposition of decitabine in aqueous solution, the reconstituted decitabine solution may only be infused to a patient for a maximum of 3 hr if the solution has been stored in the refrigerator for less than 7 hr. In addition, infusion of cold fluid can cause great discomfort and pain to the patient, which induces the patient's resistance to such a regimen.

By modifying the triazine ring and/or the ribose ring of decitabine and by formulating the compound with non-aqueous solvent, the pharmaceutical formulations can circumvent the above-listed problems associated with the current clinical treatment with decitabine. These formulations of the inventive compounds are believed to be more chemically stable than decitabine formulated in aqueous solutions containing water in at least 40% vol. of the solvent.

In a preferred embodiment, the inventive formulation contains less than 40% water in the solvent, optionally less than 20% water in the solvent, optionally less than 10% water in the solvent, or optionally less than 1% water in the solvent. In one variation, the pharmaceutical formulation is stored in a substantially anhydrous form. Optionally, a drying agent may be added to the pharmaceutical formulation to absorb water.

Owing to the enhanced stability, the inventive formulation may be stored and transported at ambient temperature, thereby significantly reducing the cost of handling the drug. Further, the inventive formulation may be conveniently stored for a long time before being administered to the patient. In addition, the inventive formulation may be diluted with regular infusion fluid (without chilling) and administered to a patient at room temperature, thereby avoiding causing patients' discomfort associated with infusion of cold fluid.

In another embodiment, the inventive compound is dissolved in glycerin at different concentrations. For example, the formulation may optionally comprise between 0.1 and 200; between 1 and 100; between 1 and 50; between 2 and 50; between 2 and 100; between 5 and 100; between 10 and 100 or between 20 and 100 mg inventive compound per ml of glycerin. Specific examples of the inventive compound per glycerin concentrations include but are not limited to 2, 5, 10, 20, 22, 25, 30, 40 and 50 mg/ml.

Different grades of glycerin (synonyms: 1,2,3-propanetriol; glycerol; glycol alcohol; glycerol anhydrous) may be used to prepare the formulations. Preferably, glycerin with chemical purity higher than 90% is used to prepare the formulations.

In another embodiment, the inventive compound is dissolved in propylene glycol at different concentrations. For example, the formulation may optionally comprise between 0.1 and 200; between 0.1 and 100; between 0.1 and 50; between 2 and 50; between 2 and 100; between 5 and 100; between 10 and 100 or between 20 and 100 mg inventive compound per ml of propylene glycol. Specific examples of decitabine per propylene glycol concentrations include but are not limited to 2, 5, 10, 20, 22, 25, 30, 40 and 50 mg/ml.

In yet another embodiment, the inventive compound is dissolved in a solvent combining glycerin and propylene glycol at different concentrations. The concentration of propylene glycol in the solvent is between 0.1–99.9%, optionally between 1–90%, between 10–80%, or between 50–70%.

In yet another embodiment, the inventive compound is dissolved at different concentrations in a solvent combining glycerin and polyethylene glycol (PEG) such as PEG300, PEG400 and PEG1000. The concentration of polyethylene glycol in the solvent is between 0.1–99.9%, optionally between 1–90%, between 10–80%, or between 50–70%.

In yet another embodiment, the inventive compound is dissolved at different concentrations in a solvent combining propylene glycol, polyethylene glycol and glycerin. The concentration of propylene glycol in the solvent is between 0.1–99.9%, optionally between 1–90%, between 10–60%, or between 20–40%; and the concentration of polyethylene glycol in the solvent is between 0.1–99.9%, optionally between 1–90%, between 10–80%, or between 50–70%.

It is believed and experimentally proven that addition of propylene glycol can further improve chemical stability, reduce viscosity of the formulations and facilitate dissolution of the inventive compound in the solvent.

The pharmaceutical formulation may further comprise an acidifying agent added to the formulation in a proportion such that the formulation has a resulting pH between about 4 and 8. The acidifying agent may be an organic acid. Examples of organic acid include, but are not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, such as hydrochloric acid, sulphuric acid, phosphoric acid, and nitric acid.

It is believed that adding an acidifying agent to the formulation to maintain a relatively neutral pH (e.g., within pH 4–8) facilitates ready dissolution of the inventive compound in the solvent and enhances long-term stability of the formulation. In alkaline solution, there is a rapid reversible decomposition of decitabine to N-(formylamidino)-N'-β-D-2-deoxyribofuranosylurea, which decomposes irreversibly to form 1-β-D-2'-deoxyribofuranosyl-3-guanylurea. The first stage of the hydrolytic degradation involves the formation of N-amidinium-N'-(2-deoxy-β-D-erythropentofuranosyl)urea formate (AUF). The second phase of the degradation at an elevated temperature involves formation of guanidine. In acidic solution, N-(formylamidino)-N'-β-D-2-deoxyribofuranosylurea and some unidentified compounds are formed. In strongly acidic solution (at pH<2.2) 5-azacytosine is produced. Thus, maintaining a relative neutral pH may be advantageous for the formulation comprising the analogs and derivatives of decitabine.

In a variation, the acidifying agent is ascorbic acid at a concentration of 0.01–0.2 mg/ml of the solvent, optionally 0.04–0.1 mg/ml or 0.03–0.07 mg/ml of the solvent.

The pH of the pharmaceutical formulation may be adjusted to be between pH 4 and pH 8, preferably between pH 5 and pH 7, and more preferably between pH 5.5 and pH 6.8.

The pharmaceutical formulation is preferably at least 80%, 90%, 95% or more stable upon storage at 25° C. for 7, 14, 21, 28 or more days. The pharmaceutical formulation is also preferably at least 80%, 90%, 95% or more stable upon storage at 40° C. for 7, 14, 21, 28 or more days.

In one embodiment, the pharmaceutical formulation of the present invention is prepared by taking glycerin and dissolving the inventive compound in the glycerin. This may be done, for example, by adding the inventive compound to the glycerin or by adding the glycerin to decitabine. By their admixture, the pharmaceutical formulation is formed.

Optionally, the method further comprises additional steps to increase the rate at which the inventive compound is solvated by the glycerin. Examples of additional steps that may be performed include, but are nor limited to, agitation, heating, extension of solvation period, and application of micronized inventive compound and the combinations thereof.

In one variation, agitation is applied. Examples of agitation include but are nor limited to, mechanical agitation, sonication, conventional mixing, conventional stirring and the combinations thereof. For example, mechanical agitation of the formulations may be performed according to manufacturer's protocols by Silverson homogenizer manufactured by Silverson Machines Inc., (East Longmeadow, Mass.).

In another variation, heat may be applied. Optionally, the formulations may be heated in a water bath. Preferably, the temperature of the heated formulations may be less than 70° C., more preferably, between 25° C. and 40° C. As an example, the formulation may be heated to 37° C.

In yet another variation, the inventive compound is solvated in glycerin over an extended period of time.

In yet another variation, a micronized form of the inventive compound may also be employed to enhance solvation kinetics. Optionally, micronization may be performed by a milling process. As an example, micronization may be performed by milling process performed Mastersizerusing an Air Jet Mill, manufactured by IncFluid Energy Aljet Inc. (Boise, IDTelford, Pa.).

Optionally, the method further comprises adjusting the pH of the pharmaceutical formulations by commonly used methods. In one variation, pH is adjusted by addition of acid, such as ascorbic acid, or base, such as sodium hydroxide. In another variation, pH is adjusted and stabilized by addition of buffered solutions, such as solution of (Ethylenedinitrilo) tetraacetic acid disodium salt (EDTA). As decitabine is known to be pH-sensitive, adjusting the pH of the pharmaceutical formulations to approximately pH 7 may increase the stability of therapeutic component.

Optionally, the method further comprises separation of non-dissolved inventive compound from the pharmaceutical formulations. Separation may be performed by any suitable technique. For example, a suitable separation method may include one or more of filtration, sedimentation, and centrifugation of the pharmaceutical formulations. Clogging that may be caused by non-dissolved particles of the inventive compound, may become an obstacle for administration of the pharmaceutical formulations and a potential hazard for the patient. The separation of non-dissolved inventive compound from the pharmaceutical formulations may facilitate administration and enhance safety of the therapeutic product.

Optionally, the method further comprises sterilization of the pharmaceutical formulations. Sterilization may be performed by any suitable technique. For example, a suitable sterilization method may include one or more of sterile filtration, chemical, irradiation, heat, and addition of a chemical disinfectant to the pharmaceutical formulation.

As noted, decitabine is unstable in water and hence it may be desirable to reduce the water content of the glycerin used for formulating the inventive compound. Accordingly, prior to the dissolution and/or sterilization step, the glycerin may be dried. Such drying of glycerin or the solution of the inventive compound in glycerin may be achieved by the addition of a pharmaceutically acceptable drying agent to the glycerin. The glycerin or the inventive formulations may be dried, for example by filtering it through a layer comprising a drying agent.

Optionally, the method may further comprise adding one or more members of the group selected from drying agents, buffering agents, antioxidants, stabilizers, antimicrobials, and pharmaceutically inactive agents. In one variation, antioxidants such as ascorbic acid, ascorbate salts and mixtures thereof may be added. In another variation stabilizers like glycols may be added.

4. Vessels or Kits Containing Inventive Compounds or Formulations

The pharmaceutical formulations, described in this invention, may be contained in a sterilized vessel such as syringes, vials or ampoules of various sizes and capacities. The sterilized vessel may optionally contain between 1–50 ml, 1–25 ml or 1–20 ml or 1–10 ml of the formulations. Sterilized vessels maintain sterility of the pharmaceutical formulations, facilitate transportation and storage, and allow administration of the pharmaceutical formulations without prior sterilization step.

The present invention also provides a kit for administering the inventive compound to a host in need thereof. In one embodiment, the kit comprises the inventive compound in a solid, preferably powder form, and a non-aqueous diluent that comprises glyercin, propylene glycol, polyethylene glycol, or combinations thereof. Mixing of the solid decitabine and the diluent preferably results in the formation of a pharmaceutical formulation according to the present invention. For example, the kit may comprise a first vessel comprising the inventive compound in a solid form; and a vessel container comprising a diluent that comprises glyercin; wherein adding the diluent to the solid inventive compound results in the formation of a pharmaceutical formulation for administering the inventive compound. Mixing the solid the inventive compound and diluent may optionally form a pharmaceutical formulation that comprises between 0.1 and 200 mg of the inventive compound per ml of the diluent, optionally between 0.1 and 100, between 2 mg and 50 mg, 5 mg and 30 mg, between 10 mg and 25 mg per ml of the solvent.

According to the embodiment, the diluent is a combination of propylene glycol and glycerin, wherein the concentration of propylene glycol in the solvent is between 0.1–99.9%, optionally between 1–90%, between 10–60%, or between 20–40%.

Also according to the embodiment, the diluent is a combination of polyethylene glycol and glycerin, wherein the concentration of polyethylene glycol in the solvent is between 0.1–99.9%, optionally between 1–90%, between 10–60%, or between 20–40%.

Also according to the embodiment, the diluent is a combination of propylene glycol, polyethylene glycol and glycerin, wherein the concentration of propylene glycol in the solvent is between 0.1–99.9%, optionally between 1–90%, between 10–60%, or between 20–40%; and the concentration of polyethylene glycol in the solvent is between 0.1–99.9%, optionally between 1–90%, between 10–60%, or between 20–40%.

The diluent also optionally comprises 40%, 20%, 10%, 5%, 2% or less water. In one variation, the dilueht is anhydrous and may optionally further comprise a drying agent. The diluent may also optionally comprise one or more drying agents, glycols, antioxidants and/or antimicrobials.

The kit may optionally further include instructions. The instructions may describe how the solid the inventive compound and the diluent should be mixed to form a pharmaceutical formulation. The instructions may also describe how to administer the resulting pharmaceutical formulation to a patient. It is noted that the instructions may optionally describe the administration methods according to the present invention.

The diluent and the inventive compound may be contained in separate vessels. The vessels may come in different sizes. For example, the vessel may comprise between 1 and 50, 1 and 25, 1 and 20, or 1 and 10 ml of the diluent.

The pharmaceutical formulations provided in vessels or kits may be in a form that is suitable for direct administration or may be in a concentrated form that requires dilution relative to what is administered to the patient. For example, pharmaceutical formulations, described in this invention, may be in a form that is suitable for direct administration via infusion.

The methods and kits described herein provide flexibility wherein stability and therapeutic effect of the pharmaceutical formulations comprising the inventive compound may be further enhanced or complemented.

5. Methods for Administrating Inventive Compounds/Compositions

The compounds/formulations of the present invention can be administered by any route, preferably in the form of a pharmaceutical composition adapted to such a route, as illustrated below and are dependent on the condition being treated. The compounds or formulations can be, for example, administered orally, parenterally, topically, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or co-administered in slow release dosage forms.

The compounds and/or compositions of this invention may be administered or co-administered in any conventional dosage form. Co-administration in the context of this invention is defined to mean the administration of more than one therapeutic agent in the course of a coordinated treatment to achieve an improved clinical outcome. Such co-administration may also be coextensive, that is, occurring during overlapping periods of time.

The inventive compound or the composition containing the inventive compound may be administered into a host such as a patient at a dose of 0.1–1000 mg/m$^2$, optionally 1–200 mg/m², optionally 1–50 mg/m², optionally 1–40 mg/m², optionally 1–30 mg/m², optionally 1–20 mg/m², or optionally 5–30 mg/m².

For example, the compound/composition of the present invention may be supplied as sterile powder for injection, together with buffering salt such as potassium dihydrogen and pH modifier such as sodium hydroxide. This formulation is preferably stored at 2–8° C., which should keep the drug stable for at least 2 years. This powder formulation may be reconstituted with 10 ml of sterile water for injection. This solution may be further diluted with infusion fluid known in the art, such as 0.9% sodium chloride injection, 5% dextrose injection and lactated ringer's injection. It is preferred that the reconstituted and diluted solutions be used within 4–6 hours for delivery of maximum potency.

In a preferred embodiment, the inventive compound/composition is administered to a patient by injection, such as subcutaneous injection, bolus i.v. injection, continuous i.v. infusion and i.v. infusion over 1 hour. Optionally the inventive compound/composition is administered to a patient via an 1–24 hour i.v. infusion per day for 3–5 days per treatment cycle at a dose of 0.1–1000 mg/m² per day, optionally at a dose of 1–100 mg/m² per day, optionally at a dose of 2–50 mg/m² per day, optionally at a dose of 10–30 mg/m² per day, or optionally at a dose of 5–20 mg/m² per day, For decitabine or azacitidine, the dosage below 50 mg/m² is considered to be much lower than that used in conventional chemotherapy for cancer. By using such a low dose of the analog/derivative of decitabine or azacitidine, transcriptional activity of genes silenced in the cancer cells by aberrant methylation can be activated to trigger downstream signal transduction, leading to cell growth arrest, differentiation and apoptosis, which eventually results in death of these cancer cells. This low dosage, however, should have less systemic cytotoxic effect on normal cells, and thus have fewer side effects on the patient being treated.

The pharmaceutical formulations may be co-administered in any conventional form with one or more member selected from the group comprising infusion fluids, therapeutic compounds, nutritious fluids, anti-microbial fluids, buffering and stabilizing agents.

As described above, the inventive compounds can be formulated in a liquid form by solvating the inventive compound in a non-aqueous solvent such as glycerin. The pharmaceutical liquid formulations provide the further advantage of being directly administrable, (e.g., without further dilution) and thus can be stored in a stable form until administration. Further, because glycerin can be readily mixed with water, the formulations can be easily and readily further diluted just prior to administration. For example, the pharmaceutical formulations can be diluted with water 180, 60, 40, 30, 20, 10, 5, 2, 1 minute or less before administration to a patient.

Patients may receive the pharmaceutical formulations intravenously. The preferred route of administration is by intravenous infusion. Optionally, the pharmaceutical formulations of the current invention may be infused directly, without prior reconstitution.

In one embodiment, the pharmaceutical formulation is infused through a connector, such as a Y site connector, that has three arms, each connected to a tube. As an example, Baxter® Y-connectors of various sizes can be used. A vessel containing the pharmaceutical formulation is attached to a tube further attached to one arm of the connector. Infusion fluids, such as 0.9% sodium chloride, or 5% dextrose, or 5% glucose, or Lactated Ringer's, are infused through a tube attached to the other arm of the Y-site connector. The infusion fluids and the pharmaceutical formulations are mixed inside the Y site connector. The resulting mixture is infused into the patient through a tube connected to the third arm of the Y site connector. The advantage of this administration approach over the prior art is that the inventive compound is mixed with infusion fluids before it enters the patient's body, thus reducing the time when decomposition of the inventive compound may occur due to contact with water. For example, the inventive compound is mixed less than 10, 5, 2 or 1 minutes before entering the patient's body.

Patients may be infused with the pharmaceutical formulations for 1, 2, 3, 4, 5 or more hours, as a result of the enhanced stability of the formulations. Prolonged periods of infusion enable flexible schedules of administration of therapeutic formulations.

Alternatively or in addition, speed and volume of the infusion can be regulated according to the patient's needs. The regulation of the infusion of the pharmaceutical formulations can be performed according to existing protocols.

The pharmaceutical formulations may be co-infused in any conventional form with one or more member selected from the group comprising infusion fluids, therapeutic compounds, nutritious fluids, anti-microbial fluids, buffering and stabilizing agents. Optionally, therapeutic components including, but are not limited to, anti-neoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies, may be co-infused with the inventive formulations.

Co-infusion in the context of this invention is defined to mean the infusion of more than one therapeutic agents in a course of coordinated treatment to achieve an improved clinical outcome. Such co-infusion may be simultaneous, overlapping, or sequential. In one particular example, co-infusion of the pharmaceutical formulations and infusion fluids may be performed through Y-type connector.

The pharmacokinetics and metabolism of intravenously administered the pharmaceutical formulations resemble the pharmacokinetics and metabolism of intravenously administered the inventive compound.

In humans, decitabine displayed a distribution phase with a half-life of 7 minutes and a terminal half-life on the order of 10–35 minutes as measured by bioassay. The volume of distribution is about 4.6 L/kg. The short plasma half-life is due to rapid inactivation of decitabine by deamination by liver cytidine deaminase. Clearance in humans is high, on the order of 126 mL/min/kg. The mean area under the plasma curve in a total of 5 patients was 408 μg/h/L with a peak plasma concentration of 2.01 μM. In patients decitabine concentrations were about 0.4 μg/ml (2 μM) when administered at 100 mg/m² as a 3-hour infusion. During a longer infusion time (up to 40 hours) plasma concentration was about 0.1 to 0.4 μg/mL. With infusion times of 40–60 hours, at an infusion rate of 1 mg/kg/h, plasma concentrations of 0.43–0.76 μg/mL were achieved. The steady-state plasma concentration at an infusion rate of 1 mg/kg/h is estimated to be 0.2–0.5 μg/mL. The half-life after discontinuing the infusion is 12–20 min. The steady-state plasma concentration of decitabine was estimated to be 0.31–0.39 μg/mL during a 6-hour infusion of 100 mg/m². The range of concentrations during a 600-mg/m² infusion was 0.41–16 μg/mL. Penetration of decitabine into the cerebrospinal fluid in man reaches 14–21% of the plasma concentration at the end of a 36-hour intravenous infusion. Urinary excretion of unchanged decitabine is low, ranging from less than 0.01% to 0.9% of the total dose, and there is no relationship between excretion and dose or plasma drug levels. High clearance values and a total urinary excretion of less than 1% of the administered dose suggest that decitabine is eliminated rapidly and largely by metabolic processes.

Owing to their enhanced stability in comparison with decitabine, the inventive compounds/compositions can enjoy longer shelf life when stored and circumvent problems associated with clinical use of decitabine. For example, the inventive compounds may be supplied as lyophilized powder, optionally with an excipient (e.g., cyclodextrin), acid (e.g., ascorbic acid), alkaline (sodium hydroxide), or buffer salt (monobasic potassium dihydrogen phosphate). The lyophilized powder can be reconstituted with sterile water for injection, e.g., i.v., i.p., i.m., or subcutaneously. Optionally, the powder can be reconstituted with aqueous or non-aqueous solvent comprising a water miscible solvent such as glycerin, propylene glycol, ethanol and PEG. The resulting solution may be administered directly to the patient, or diluted further with infusion fluid, such as 0.9% Sodium Chloride; 5% Dextrose; 5% Glucose; and Lactated Ringer's infusion fluid.

The inventive compounds/compositions may be stored under ambient conditions or in a controlled environment, such as under refrigeration (2–8° C.; 36–46° F.). Due to their superior stability in comparison with decitabine, the inventive compounds/compositions can be stored at room temperature, reconstituted with injection fluid, and administered to the patient without prior cooling of the drug solution.

In addition, due to their enhanced chemical stability, the inventive compound/composition should have a longer plasma half-life compared to that of decitabine. Thus, the inventive compound/composition may be administered to the patient at a lower dose and/or less frequently than that for decitabine.

6. Combination Therapy with Inventive Pharmaceutical Compositions

The pharmaceutical formulations of the present invention may be used in conjunction with therapeutic components including but not limiting to anti-neoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies.

In one embodiment, an alkylating agent is used in combination with and/or added to the inventive compound/formulation. Examples of alkylating agents include, but are not limited to bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), non-classic alkylating agents (altretamine, dacarbazine, and procarbazine), platinum compounds (carboplastin and cisplatin).

In another embodiment, cisplatin, carboplatin or cyclophosphamide is used in combination with and/or added to the inventive compound/formulation.

In another embodiment, a member of the retinoids superfamily is used in combination with and/or added to the inventive compound/formulation. Retinoids are a family of structurally and functionally related molecules that are derived or related to vitamin A (all-trans-retinol). Examples of retinoid include, but are not limited to, all-trans-retinol, all-trans-retinoic acid (tretinoin), 13-cis retinoic acid (isotretinoin) and 9-cis-retinoic acid.

In yet another embodiment, a hormonal agent is used in combination with and/or added to the inventive compound/formulation. Examples of such a hormonal agent are synthetic estrogens (e.g. diethylstibestrol), antiestrogens (e.g. tamoxifen, toremifene, fluoxymesterol and raloxifene), anti-androgens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

In yet another embodiment, a plant-derived agent is used in combination with and/or added to the inventive compound/formulation. Examples of plant-derived agents include, but are not limited to, vinca alkaloids (e.g., vincristine, vinblastine, vindesine, vinzolidine and vinorelbine), camptothecin (20(S)-camptothecin, 9-nitro-20(S)-camptothecin, and 9-amino-20(S)-camptothecin), podophyllotoxins (e.g., etoposide (VP-16) and teniposide (VM-26)), and taxanes (e.g., paclitaxel and docetaxel).

In yet another embodiment, a biologic agent is used in combination with and/or added to the inventive compound/formulation, such as immuno-modulating proteins such as cytokines, monoclonal antibodies against tumor antigens, tumor suppressor genes, and cancer vaccines.

Examples of interleukins that may be used in combination with and/or added to the inventive compound/formulation include, but are not limited to, interleukin 2 (IL-2), and interleukin 4 (IL-4), interleukin 12 (IL-12). Examples of interferons that may be used in conjunction with decitabine—glycerin formulations include, but are not limited to, interferon α, interferon β (fibroblast interferon) and interferon γ (fibroblast interferon). Examples of such cytokines include, but are not limited to erythropoietin (epoietin), granulocyte-CSF (filgrastim), and granulocyte, macrophage-CSF (sargramostim). Immuno-modulating agents other than cytokines include, but are not limited to bacillus Calmette-Guerin, levamisole, and octreotide.

Example of monoclonal antibodies against tumor antigens that can be used in conjunction with the inventive formulations include, but are not limited to, HERCEPTIN® (Trastruzumab), RITUXAN® (Rituximab), MYLOTARG® (anti-CD33), and CAMPATH® (anti-CD52).

7. Indications for Compounds or Pharmaceutical Compositions of the Present Invention The pharmaceutical formulations according to the present invention may be used to treat a wide variety of diseases that are sensitive to the treatment with decitabine.

Preferable indications that may be treated using the pharmaceutical formulations of the present invention include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), muscular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In another embodiment, the pharmaceutical formulations of the present invention may be used for treating diseases associated with undesired or abnormal angiogenesis. The method comprises administering to a patient suffering from undesired or abnormal angiogenesis the pharmaceutical formulations of the present invention alone, or in combination with anti-neoplastic agent whose activity as an anti-neoplastic agent in vivo is adversely affected by high levels of DNA methylation. The particular dosage of these agents required to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the pharmaceutical formulations of the present invention may be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical bums, bacterial ulcers, fungal ulcers, Herpes simplex infections, Herpes zoster infections, protozoan infections and Kaposi sarcoma.

In yet another embodiment, the pharmaceutical formulations of the present invention may be used for treating chronic inflammatory diseases associated with abnormal angiogenesis. The method comprises administering to a patient suffering from a chronic inflammatory disease associated with abnormal angiogenesis the pharmaceutical formulations of the present invention alone, or in combination with an anti-neoplastic agent whose activity as an anti-neoplastic agent in vivo is adversely affected by high levels of DNA methylation. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the pharmaceutical formulations of the present invention may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present invention should inhibit the formation of the sprouts and prevent the formation of granulomas. The inflammatory bowel diseases also exhibit extra intestinal manifectations, such as skin lesions. Such lesions are characterized by inflammation and angiogenesis and can occur at many sites other the gastrointestinal tract. Inhibition of angiogenesis by the pharmaceutical formulations of the present invention should reduce the influx of inflammatory cells and prevent the lesion formation.

Sarcoidois, another chronic inflammatory disease, is characterized as a multi-system granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the pharmaceutical formulations of the present invention to inhibit angionesis, such granulomas formation can be inhibited. Psoriasis, also a chronic and recurrent inflammatory disease, is characterized by papules and plaques of various sizes. Treatment using the pharmaceutical formulations of the present invention should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the pharmaceutical formulations of the present invention alone or in conjunction with other anti-RA agents may prevent the formation of new blood vessels necessary to maintain the chronic inflammation and provide the RA patient relief from the symptoms.

In yet another embodiment, the pharmaceutical formulations of the present invention may be used for treating diseases associated with abnormal hemoglobin synthesis. The method comprises administering the pharmaceutical formulations of the present invention to a patient suffering from disease associated with abnormal hemoglobin synthesis. Decitabine containing formulations stimulate fetal hemoglobin synthesis because the mechanism of incorporation into DNA is associated with DNA hypomethylation. Examples of diseases associated with abnormal hemoglobin synthesis include, but are not limited to, sickle cell anemia and β-thalassemia.

In yet another embodiment, the pharmaceutical formulations of the present invention may be used to control intracellular gene expression. The method comprises administering the pharmaceutical formulations of the present invention to a patient suffering from disease associated with abnormal levels of gene expression. DNA methylation is associated with the control of gene expression. Specifically, methylation in or near promoters inhibit transcription while demethylation restores expression. Examples of the possible applications of the described mechanisms include, but are not limited to, therapeutically modulated growth inhibition, induction of apoptosis, and cell differentiation.

Gene activation facilitated by the pharmaceutical formulations of the present invention may induce differentiation of cells for therapeutic purposes. Cellular differentiation is induced through the mechanism of hypomethylation. Examples of morphological and functional differentiation include, but are not limited to differentiation towards formation of muscle cells, myotubes, cells of erythroid and lymphoid lineages.

Although exemplary embodiments of the present invention have been described and depicted, it will be apparent to the artisan of ordinary skill that a number of changes, modifications, or alterations to the invention as described herein may be made, none of which depart from the spirit of the present invention. All such changes, modifications, and alterations should therefore be seen as within the scope of the present invention.

EXAMPLE

The following are examples of the compounds and methods of synthesis thereof according to the present invention.

1. Derivatives of Decitabine or Azacitidine with 4- and 6-Position Substitution

In this example, the analogs of decitabine or azacitidine modified at the 4- and 6-position are described. As discussed in detail above, based on their resonance analysis of decitabine and azacitidine the inventors believe that introduction of a chemical group into certain position of decitabine is expected to increase aqueous stability of decitabine.

Figure 4A:
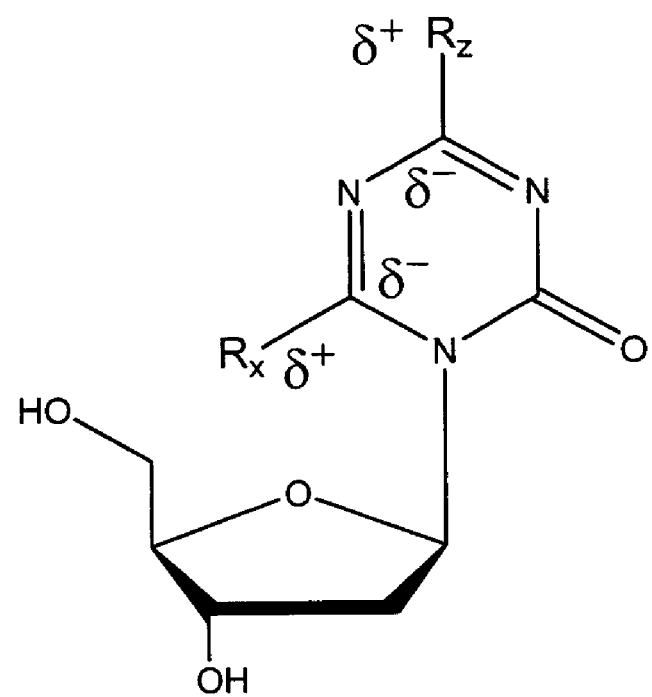
FIG. 4A illustrates the strategy of modifying the 4- and 6-position of the triazine ring of decitabine in order to improve its chemical and physiological stability.

For example, as shown in FIG. 4A, electron-donating groups (+I) can decrease electrophilicity of the 6-position. Replacement of the 6-position hydrogen ($R_x$) of 5-azacytidine with a field-effect electron-donating group (+I) lowers the surrounding electrophilicity and prevents hydrolytic cleavage at the 6-position of the triazine ring. Similarly, substitution of the 4-position ($R_z$) with varying electron-donating groups ($NH_2$, $NR_2$>OH, OR>halogen>alkyl>H) reduces electrophilicity of the 6-position, while electron-withdrawing groups ($NO_2$, $NR_3^+$, $CF_3$, $Cl_3$>HC=O, R—C=O, $CO_2H$, $CO_2R$, $SO_3H$, CN>H) increases the electrophilicity of the 6-position.

Figure 4B:
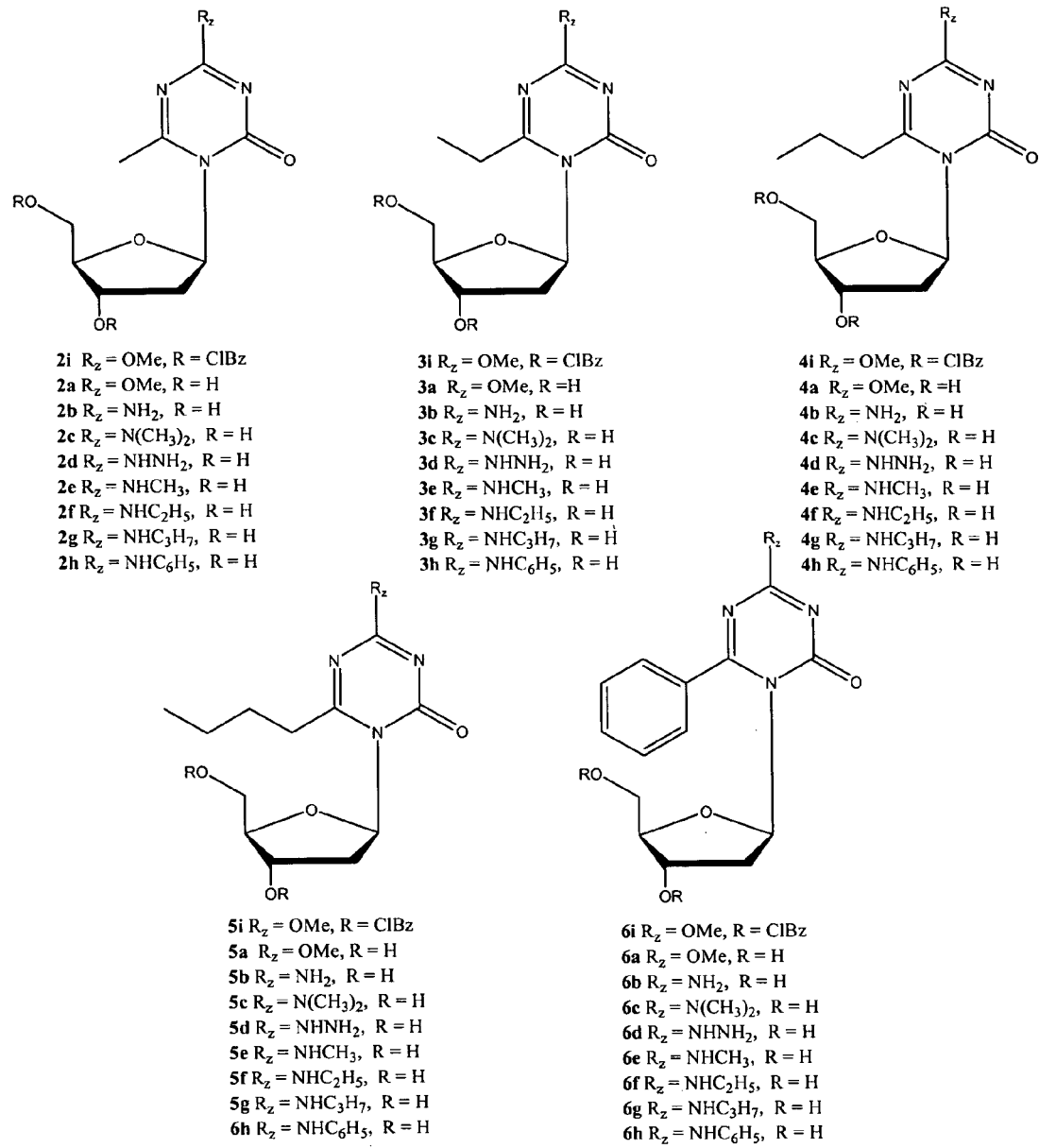
FIGS. 4B–D illustrate examples of decitabine analogs with modifications in the 4- and/or 6-position of the triazine ring, as well as in the 2'-deoxyribose ring.
Figure 4C:
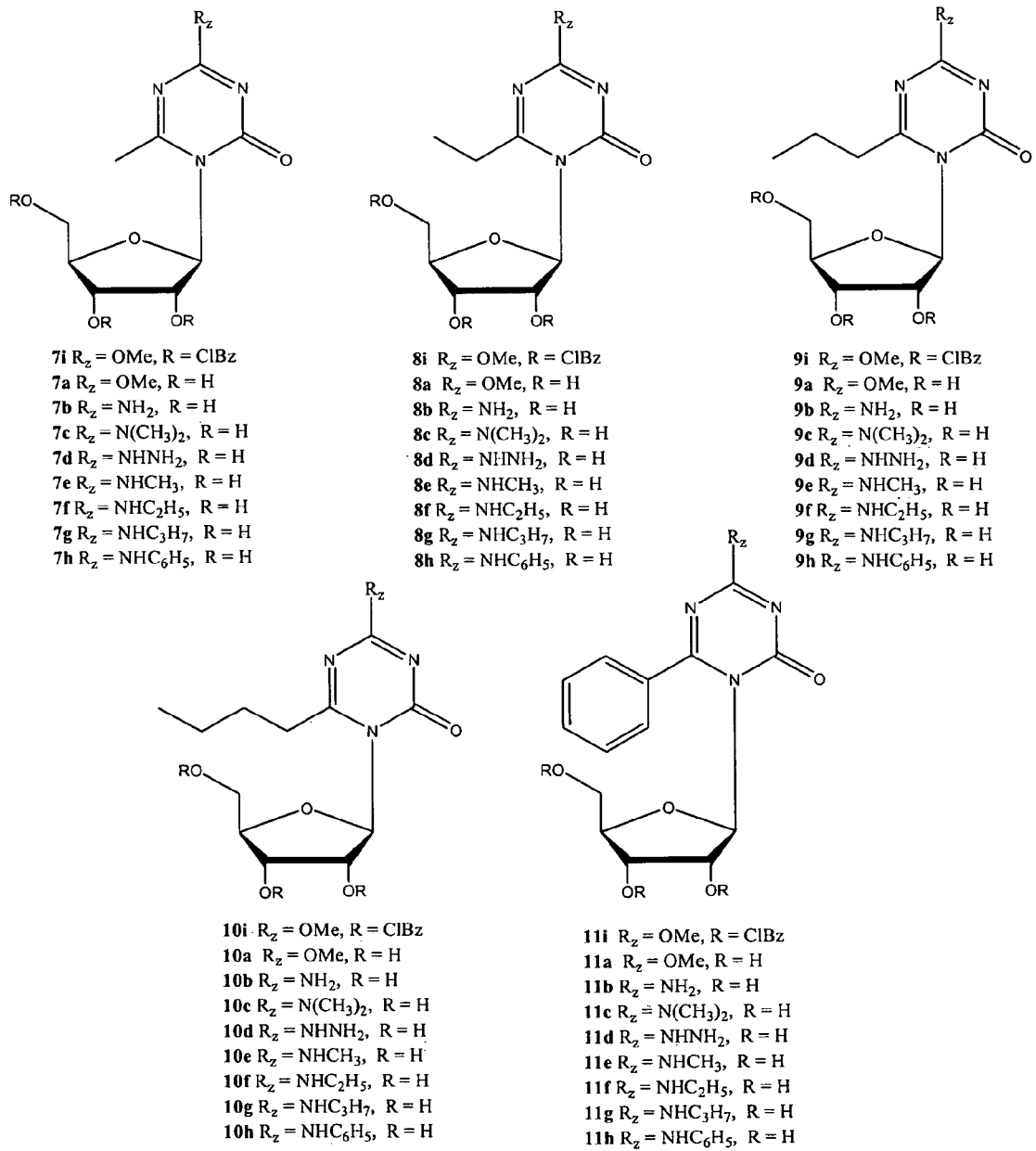

While the 6-position can be modified by any electron-donating alkyl group, it is desirable to stabilize the 6-position against hydrolysis without interfering with the biological activity of decitabine. As the length and size of the alkyl increase (FIG. 4B), it is possible that the decitabine analogs may exist in conformations that are not favorable for binding with DNA methyltransferase. Due to steric crowding, the alkyl group may limit the analogs to certain conformations, and those may not necessarily be favorable for binding with DNA methyltransferase. Therefore, it is preferred that a compromise is made between stability against hydrolysis and binding affinity toward DNA methyltransferase. FIG. 4B and FIG. 4C list the preferred alkyl derivatives of decitabine and azacitidine, respectively, that are made by substituting the hydrogen at the 6-position with a $CH_3$, $CH_2CH_3$, $CH_2CH_2CH_3$, $CH_2CH_2CH_2CH_3$, and phenyl group.

Figure 4D:
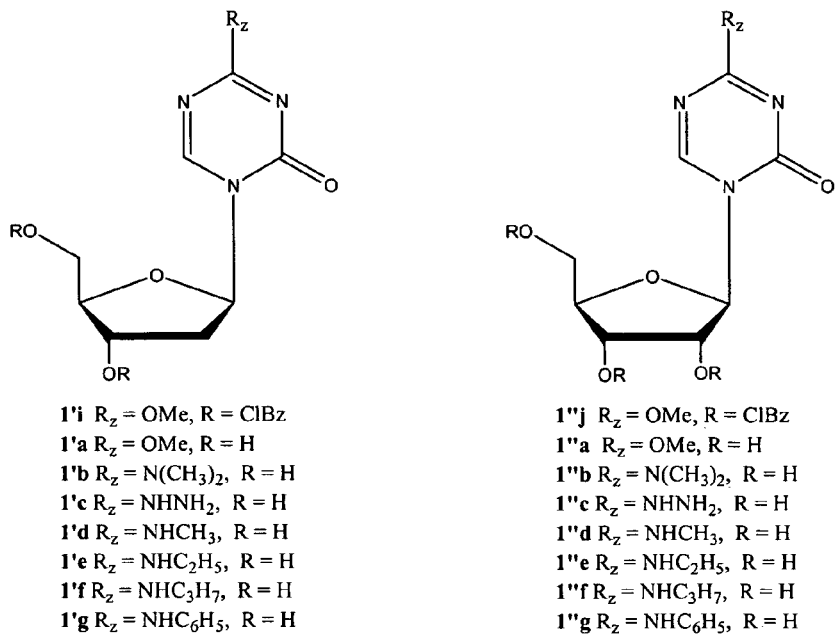
Figure 4E:
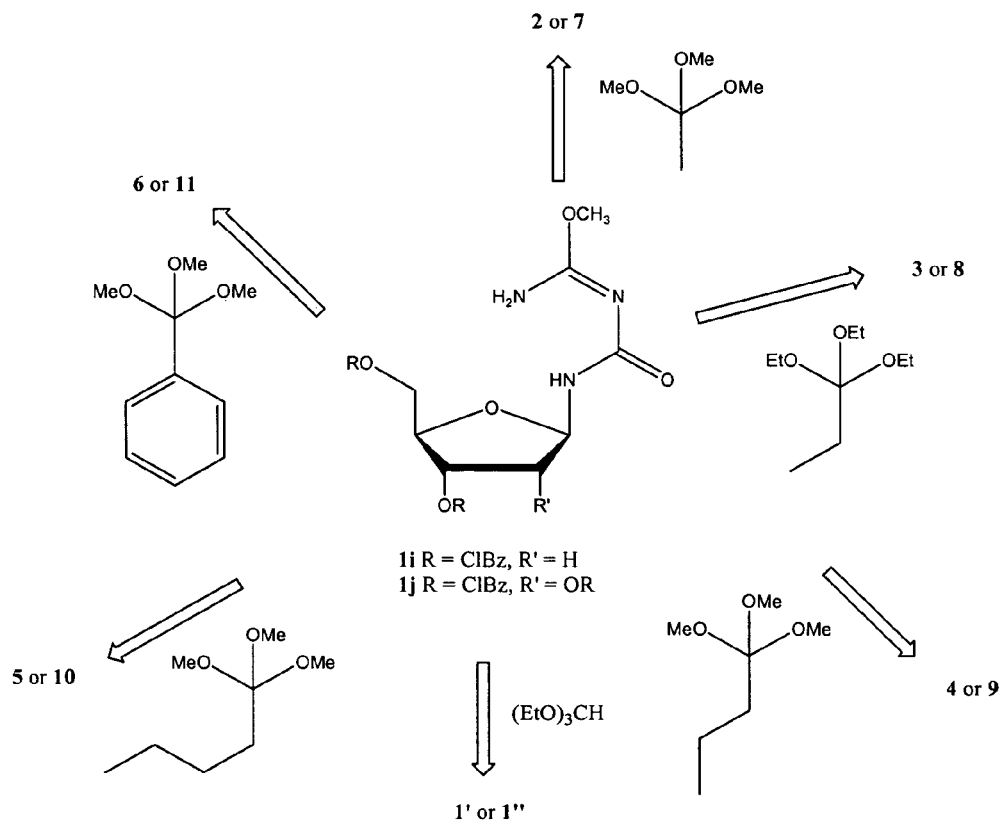
FIG. 4E illustrates schemes for synthesis of various analogs or derivatives of decitabine and azacitidine.
Figure 4F:
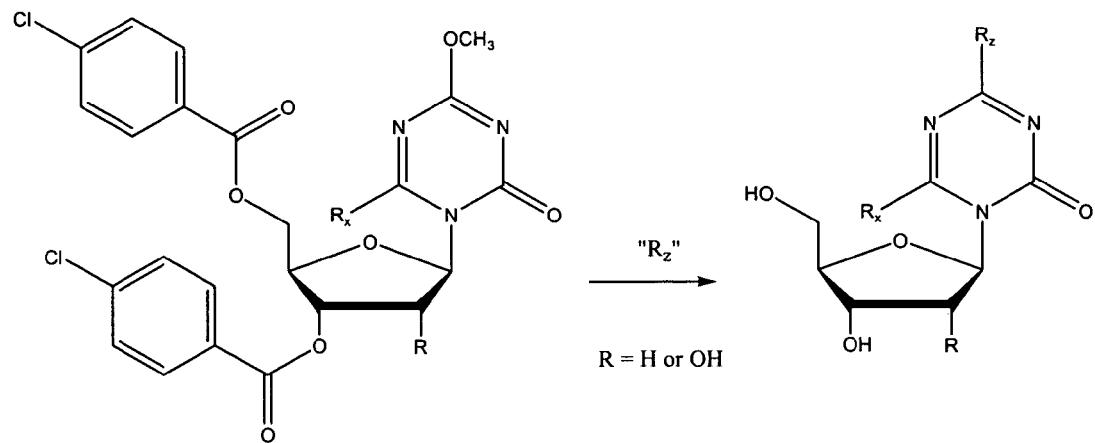
FIG. 4F illustrates a scheme for modifying the 4-position of an analog of decitabine or azacitidine.

Synthesis of these alkyl-derivatives of decitabine can be achieved by using a modified procedure based on Pliml, J. et al. Pliml, J.; Sorm, F. *Collect. Czech. Chem. Commun.* 1964, 29, 2576–2577. Specifically the Pliml synthesis procedure can be modified at the cyclization of 1-(2-deoxy-3, 5-di-O-p-chlorobenzoyl-D-ribofuranosyl)-4-O-methylisobiuret (1i, 4E) to yield the alkyl derivatives of decitabine. FIG. 4D illustrates this modification, which gives decitabine derivatives 2, 3, 4, 5 and 6 after deprotection.

In one embodiment, for example, azacytidine derivatives 2, 3, 4, 5 or 6 was prepared by stirring and refluxing (~90° C.) a mixture of 1 '-(2'-Deoxy-3'5'-di-O-p-chlorobenzoyl-D-ribofuranosyl)-4-O-methylisobiruet (1i) in formic acid (1.5 eq.) and 50 equivalents of trimethyl orthoacetate, triethyl orthopropionate, trimethyl orthobutyrate, trimethyl orthovalerate, or trimethyl orthobenzoate, respectively, until complete reaction (<5% 1i remaining) as determined by HPLC. The reaction was cooled to 22±5° C. before charging slowly (in a period of not less than 2 hours) with water (not less than 3 kg of water per mole of 1i used) to precipitate the respective fully protected intermediate 2i, 3i, 4i, 5 or 6i (FIGS. 4B and 4C). The mixture was stirred for an additional one hour before it was cooled to 5±5° C. and stirred for two hours. The slurry was filtered and the solid cake was dried in vacuo at 50±5° C. until loss on drying (LOD) was less than 0.1%. The dried intermediate was suspended in a mixture of anhydrous methanol (~21 liters per mole of intermediate used) and anhydrous ammonia gas, dimethylamine, hydrazine, methylamine, ethylamine, propylamine or benzylamine (~22 eq.), and the mixture was stirred for not less than 48 hours and until complete consumption of intermediate product. After reaction completion excess volatile reagent such as ammonia and dimethylamine was removed by application of a slight vacuum for one hour before the mixture was concentrated in vacuo at 50±5° C. to a minimal volume (~6 liters per mole of intermediate used) and cool to 5±5° C. initiate crystallization of the crude 2b–h, 3b–h, 4b–h, 52b–h or 6b–h. The crude product was filtered after 1 hour, washed with cold (5° C.) methanol (0.5 liter per mole of intermediate used), re-dissolved in hot (42° C.) anhydrous methanol (33 liters per mole of intermediate used), decolorized with activated carbon (equivalent to 24 g per mole of intermediate used), filtered to obtain a clear solution of product, concentrated in vacuo at not more than 50° C. to a minimal volume (~2 liters mole per of intermediate used), and allowed to crystallize at 22±5° C. for ~12 hours. The slurry was filtered, the crystalline product washed with methanol (0.2 liter per mole of intermediate used), and the pure product 2b–h, 3b–h, 4b–h, 5b–h or 6b–h dried in vacuo at not more than 40° C. for ~8 hours.

Azacitidine derivatives 7b–h, 8b–h, 9b–h, 10b–h and 11b–h can likewise be synthesized starting from a similarly protected ribose derivative such as 1'-(2', 3', 5'-tri-O-p-chlorobenzoyl-D-ribofuranosyl)-4-O-methylisobiruet via intermediates 7i, 8i, 9i, 10i and 11i prior to deprotection (FIG. 4C).

Decitabine derivatives 1'b–g and azacitidine derivatives 1'''b–g can likewise be synthesized starting from a similarly protected ribose derivative such as 1 '-(2', 3', 5'-tri-O-p-chlorobenzoyl-D-ribofuranosyl)-4-O-methylisobiruet via intermediates 1'i and 1'''i (FIG. 4D), respectively.

Decitabine derivatives 1'a, 1'''a, 2a, 3a, 4a, 5a, 6a, 7a, 8a, 9a, 10a and 11a can be synthesized from the respective 1'i, 1'''i, 2i, 3i, 4i, 5i, 6i, 7i, 8i, 9i, 10i and 11i by treating with sodium methoxide or tertiary amine (which includes but is not limited to triethylamine, ethyl diisopropylamine and DBU) to remove the 3', 5'-di-O-p-chlorobenzoyl protection without affecting the 4-OMe group.

2. Keto-Enol Derivatives of Decitabine or Azacitidine at the 6-Position

Figure 5A:
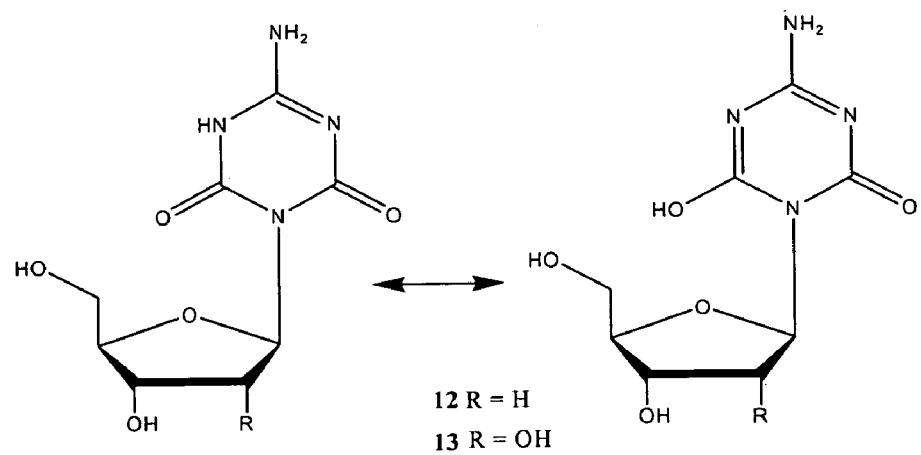
FIG. 5A illustrates a scheme for modification of the N=CH functional group of the triazine ring of decitabine or azacitidine.

In this example, the N=CH functional group of the triazine ring of decitabine or azacitidine is replaced with a more stable NH—C=O⇌N=C—OH moiety, producing keto-enol derivatives 12 and 13 are obtained (FIG. 5A). This moiety is resistant to hydrolytic cleavage in aqueous conditions. In a basic medium where decitabine is easily hydrolyzed, the OH group of the keto-enol analog becomes the strong electron-donating (+I) group O⁻, which will prevent hydrolytic cleavage of the triazine ring.

Figure 5B:
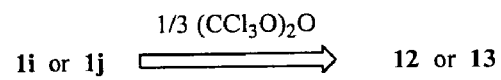
FIG. 5B illustrates a scheme for synthesis of keto-enol derivatives of decitabine or azacitidine.

The keto-enol derivative of decitabine or azacytiding can be synthesized by cyclizing 1-(2-deoxy-3,5-di-O-p-chlorobenzoyl-D-ribofuranosyl)-4-O-methylisobiuret (1i) with one-third equivalent of triphosgene (or one-half equivalent of oxalyl chloride) to give the keto-enol 12 after deprotection (FIG. 5B). The azacytidine derivative 13 can likewise be synthesized.

In one embodiment, for example, 1'-(2'-deoxy-3',5'-di-O-p-chlorobenzoyl-D-ribofuranosyl)-4-O-methylisobiuret (1i) or 1'-(2',3',5'-tri-O-p-chlorobenzoyl-D-ribofuranosyl)-4-O-methylisobiruet (1j) was dissolved (0.001 to 10 M concentration) in an anhydrous aprotic organic solvent effective in solubilizing it. These solvents include, but are not limited to: acetonitrile; chlorobenzene; dichloromethane; 1,2-dichloroethane; methylcyclohexane; N-methylpyrrolidone; nitromethane; acetone; DMSO; ethyl acetate; ethyl ether; and ethyl formate. To this solution was added triphosgene (0.4 to 5 eq.), and the mixture was stirred at 23° C. until complete reaction as determined by HPLC (<5% 1i or 1j remaining) or TLC. The reaction mixture was washed with saturated bicarbonate (enough to neutralize any generated HCl), the organic layer dried with sodium or magnesium sulfate (until no clumps form), filtered, concentrated, and dried in vacuo at not more than 50° C. until loss on drying (LOD) was less than 0.1%. The dried intermediate was suspended in a mixture of anhydrous methanol (~21 liters per mole of intermediate used) and anhydrous ammonia gas (~22 eq.), and the mixture was stirred for not less than 48 hours and until complete consumption of intermediate product. After reaction completion excess ammonia was removed by application of a slight vacuum for one hour before the mixture was concentrated in vacuo at 50±5° C. to a minimal volume (~6 liters per mole of intermediate used) and cool to 5±5° C. initiate crystallization of the crude product. The crude product was filtered after 1 hour, washed with cold (5° C.) methanol (0.5 liter per mole of intermediate used), dissolved in hot (42° C.) anhydrous methanol (33 liters per mole of intermediate used), decolorized with activated carbon (equivalent to 24 g per mole of intermediate used), filtered to obtain a clear solution of product, concentrated in vacuo at not more than 50° C. to a minimal volume (~2 liters per mole of intermediate used), and allowed to crystallize at 22±5° C. for ~12 hours. The slurry was filtered, the crystalline product washed with methanol (0.2 liter per mole of intermediate used), and the pure product 12 or 13 dried in vacuo at not more than 40° C. for ~8 hours.

3. Hydrogen and Halogen Derivatives of Decitabine or Azacitidine

In this example, one or more of the 1'-5' position in the ribose ring of decitabine or azacitidine ($R_1$-$R_6$, FIG. 6A) are replaced with a halogen (H, F, Cl, Br, I, or $CF_3$)

Figure 6A:
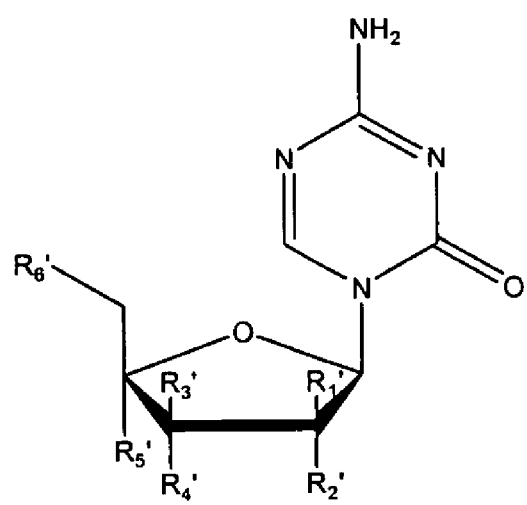
FIG. 6A illustrates a scheme for modifying the 1'–6'-position of decitabine or azacitidine.
Figure 6B:
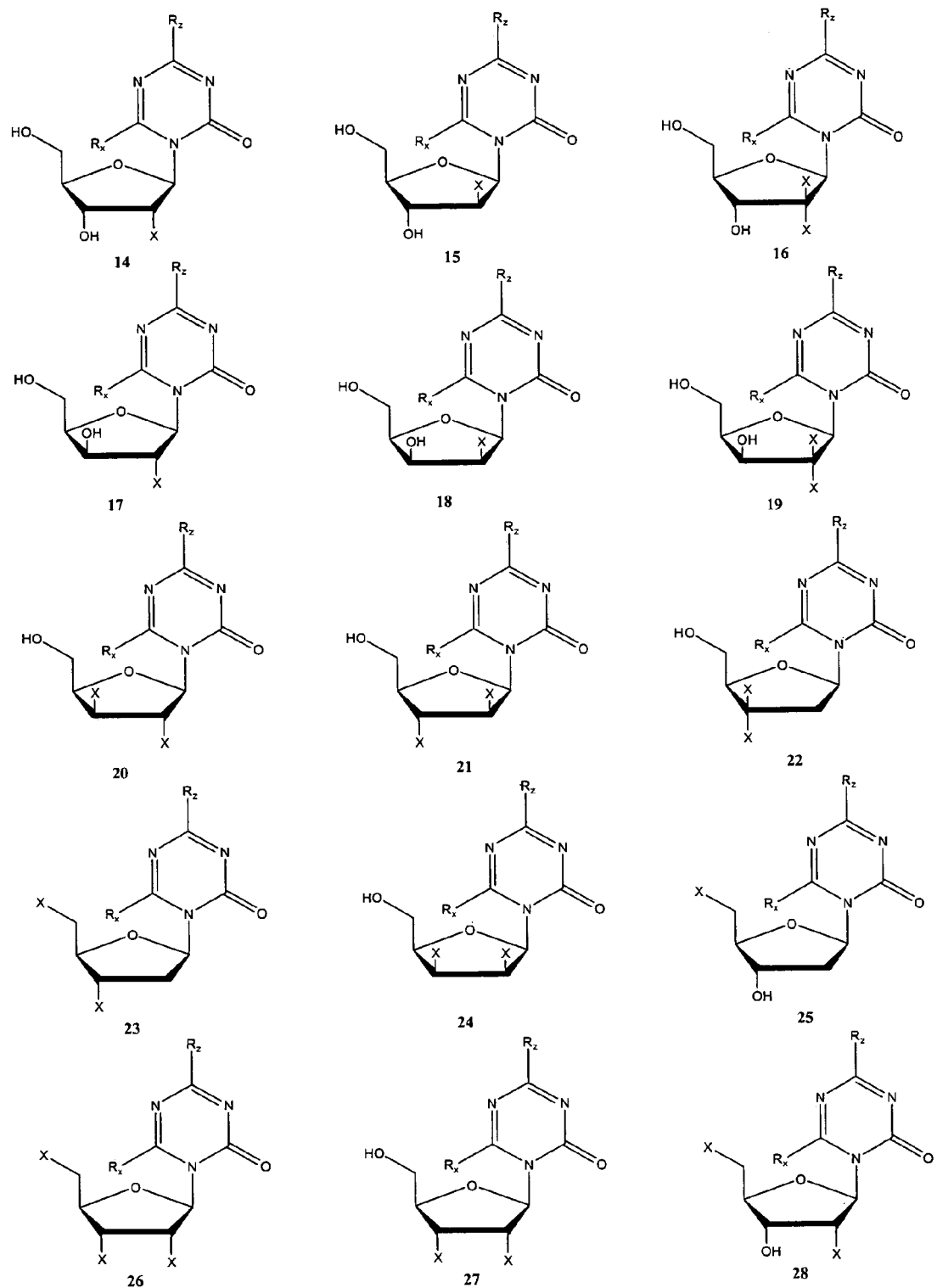
FIGS. 6B–C illustrate examples of decitabine or azacitidine analogs with modifications in the 4- and/or 6-position of the triazine ring, as well as in the deoxyribose or ribose ring.
Figure 6C:
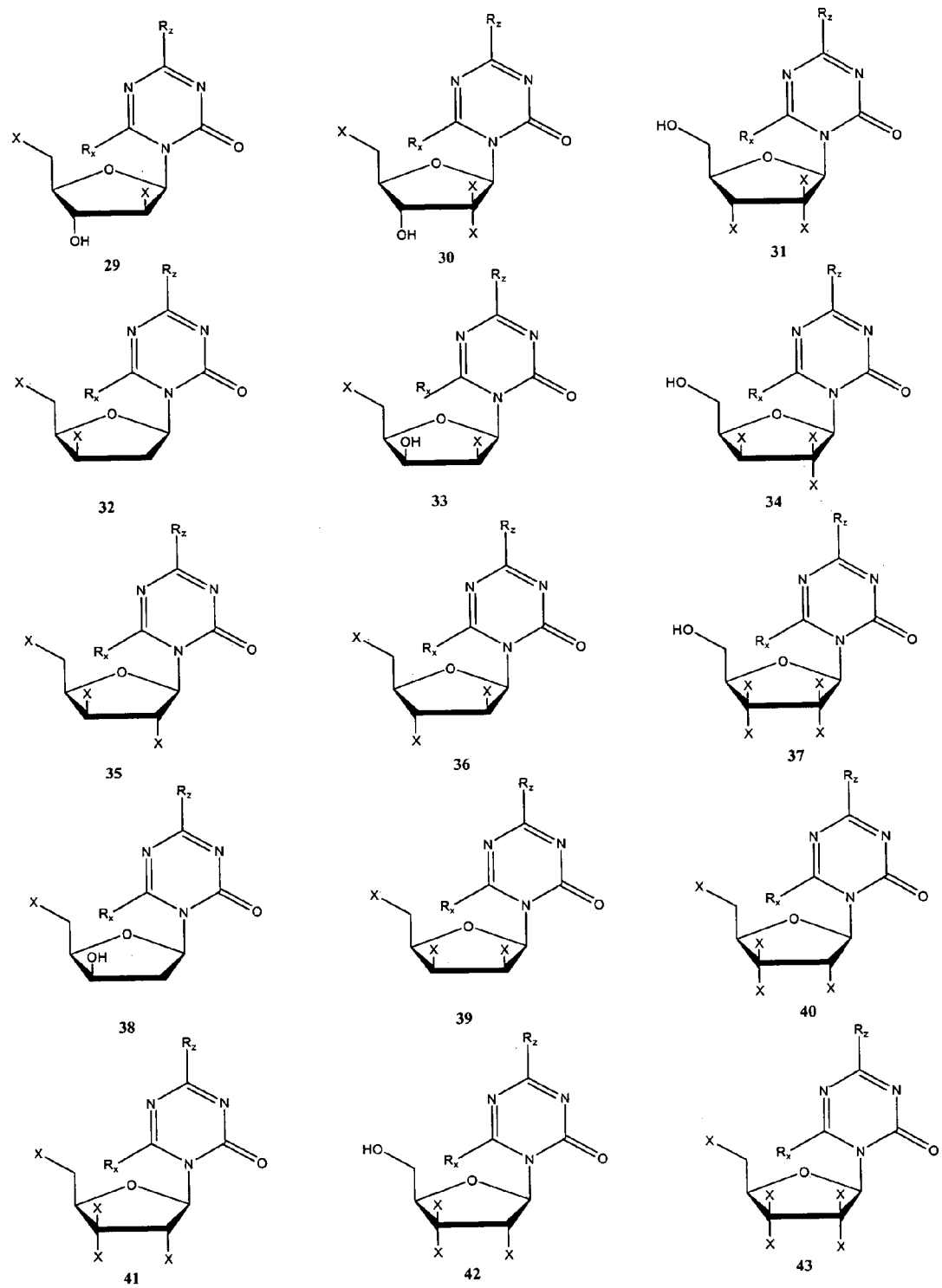

The inventors believe that introducing halogen into decitabine should prevent hydrolytic and oxidative cleavage from occurring. When introduced onto the sugar ring, the electronegativity of the field-effect electron-withdrawing (−I) halogens lowers the surrounding electron density and prevents oxidative cleavage of the sugar moiety. For this reason, halogen derivatives, especially fluorine, are highly desirable. One additional benefit of fluorine derivatives is that the fluorine atom is so small that there is no distinct stereoscopic difference between the C—H bond and the C—F bond, which allows fluorine derivatives to mimic natural C—H bond and be easily incorporated into the metabolic pathway of living organisms. FIG. 6A illustrates the positions where hydrogen or halogen substitution can be incorporated. FIGS. 6B and 6C list a series of halogenated derivatives that will be made, where X is preferably H, F, Cl, Br, I or $CF_3$.

Figure 6D:
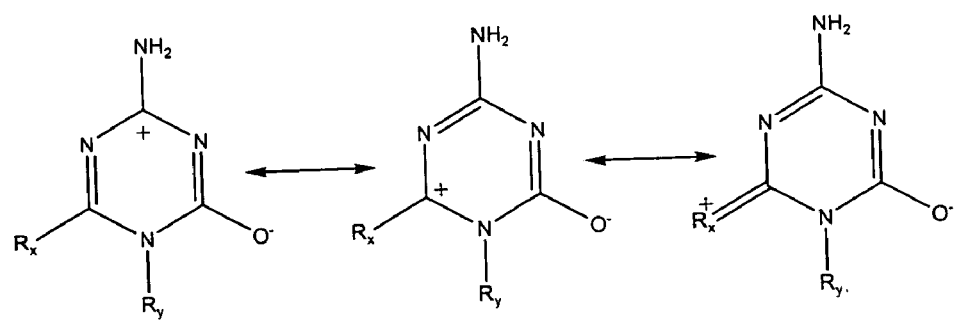
FIG. 6D illustrates electron resonance analysis of the triazine ring with modifications in the 6-position.
Figure 6E:
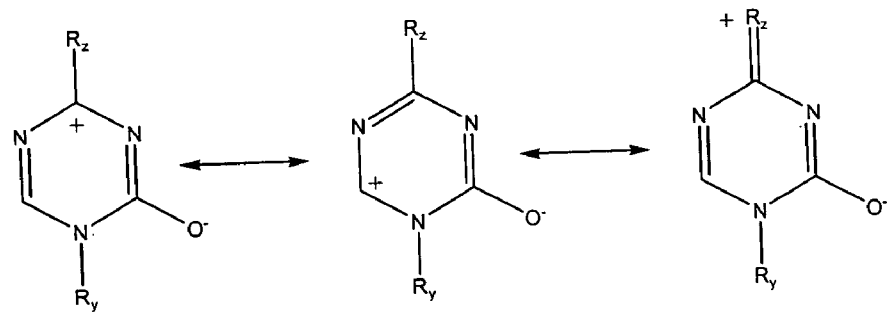
FIG. 6E illustrates electron resonance analysis of the triazine ring with modifications in the 4-position.

Halogen such as F, Cl, Br and I are not only field-effect electron-withdrawing (−I) groups but also resonance-effect electron-donating (+M) groups. In a conjugated system like the triazine ring, the resonance-effect of halogens may stabilize the 6-position and prevent oxidative and hydrolytic cleavage of the ring (FIG. 6D).

Figure 7A:
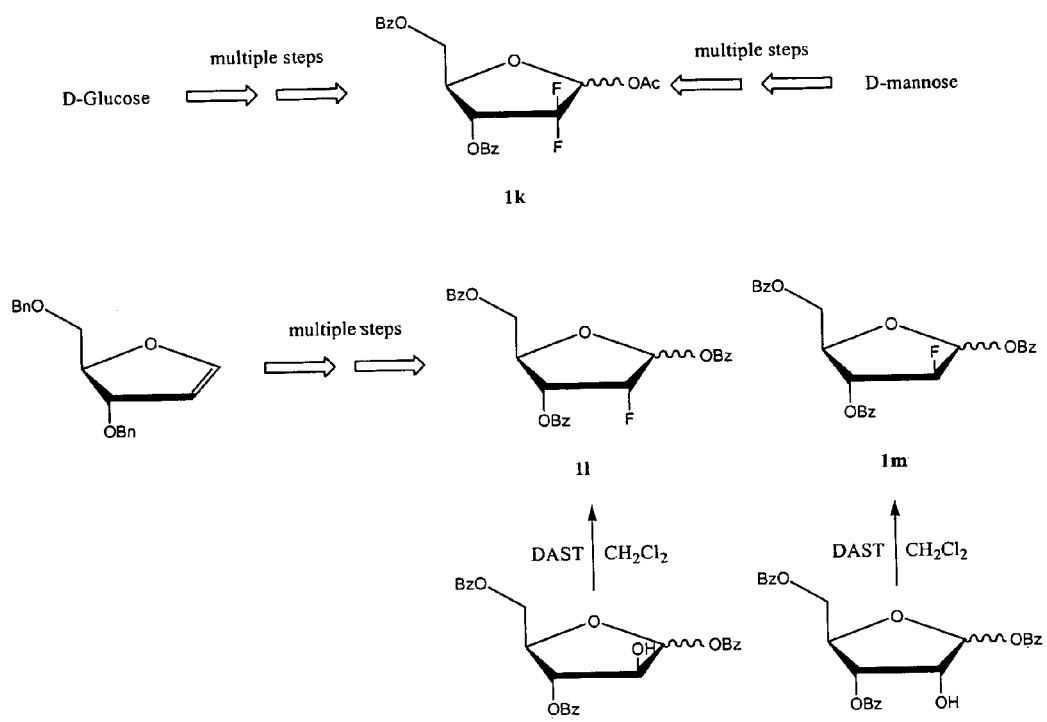
FIG. 7A illustrates a scheme for synthesis of halogen derivatives of decitabine by using halogenated pentose and triazine precursors.

The halogen derivatives of decitabine can be synthesized by using halogenated pentose and triazine precursors. These precursors can be synthesized by using pre-existing or modified methods known in the art. For example, the precursor 1-O-acetyl-2-deoxy-3,5-di-O-benzoyl-2,2-difluoro-D-ribose 1k can be obtained from inexpensive D-glucose and D-mannose (FIG. 7A). Fernández, R.; Matheu, M. I.; Echarri, R.; Castillón, S. Tetrahedron 1998, 54, 3523–3532. Other mono-fluorinated ribose derivatives can be obtained from suitably protected ribose. Dax, K.; Albert, M.; Ortner, J.; Paul, B. J. Carbohydr. Res. 2000, 327, 47–86. Pankiewiz; K. W. Carbohydr. Res. 2000,327, 87–105.

In one embodiment, for example, a 1.0:1.5:3.0 molar mixture of 1-O-acetyl-2-deoxy-3,5-di-O-benzoyl-2,2-difluoro-D-ribose (1k); 2-[(trimethylsilyl)amino]-4-[(trimethylsilyl)oxy]-s-triazine (1n); $SnCl_4$ in anhydrous mixture of acetonitrile-1,2-dichloroethane (3.0: 1.0, v/v, at a concentration of 50 mM 1k) was refluxed for not less than 3 hours or until complete reaction as determined by HPLC (<5% 1k remaining) or TLC. The reaction mixture was diluted with 1,2-dichloroethane, washed with cold saturated bicarbonate, the organic layer dried with sodium or magnesium sulfate (until no clumps form), filtered, concentrated, and dried in vacuo at not more than 50° C. until loss on drying (LOD) was less than 0.1%. The dried intermediate was suspended in a mixture of anhydrous methanol (~21 liters per mole of intermediate used) and anhydrous ammonia gas (~22 eq.), and the mixture was stirred for not less than 48 hours and until complete consumption of intermediate product. After reaction completion excess ammonia was removed by application of a slight vacuum for one hour before the mixture was concentrated in vacuo at 50±5° C. to a minimal volume (~6 liters per mole of intermediate used) and cool to 5±5° C. initiate crystallization of the crude product. The crude product was filtered after 1 hour, washed with cold (5° C.) methanol (0.5 liter per mole of intermediate used), dissolved in hot (42 C) anhydrous methanol (33 liters per mole of intermediate used), decolorized with activated carbon (equivalent to 24 g per mole of intermediate used), filtered to obtain a clear solution of product, concentrated in vacuo at not more than 50° C. to a minimal volume (~2 liters per mole of intermediate used), and allowed to crystallize at 22±5° C. for ~12 hours. The slurry was filtered, the crystalline product washed with methanol (0.2 liter per mole of intermediate used), and the pure product 16 (where X=F) dried in vacuo at not more than 40° C. for ~8 hours.

Figure 7B:
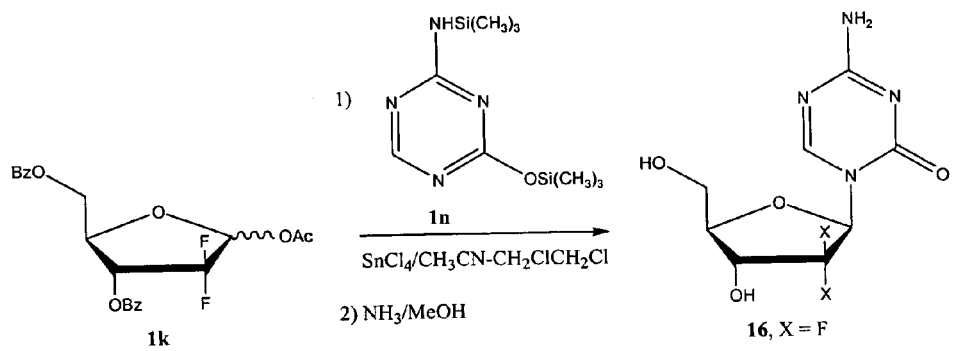
FIG. 7B illustrates a scheme for synthesis of halogen derivatives of azacitidine.

Azacytidine derivatives 14 and 15 (FIG. 6B) can likewise be synthesized by coupling similarly protected fluoro-ribose derivatives such as 1l and 1m (FIG. 7B) with 2-[(trimethylsilyl)amino]-4-[(trimethylsilyl)oxy]-s-triazine (1n) in the presence of $SnCl_4$ in acetonitrile-1,2-dichloroethane.

In some embodiment, other Lewis acids (which include, but are not limited to: TMSOTf, $BX_3$, $AlX_3$, $FeX_3$, $GaX_3$, $SbX_5$, $SnX_4$, $AsX_5$, $ZnX_2$, and $HgX_2$, where X is a halogen) in the range of 0.1 to 3 molar equivalents can be used to facilitate coupling between protected fluoro-ribose derivatives and 2-[(trimethylsilyl)amino]-4-[(trimethylsilyl)oxy]-s-triazine (1n).

Figure 7C:
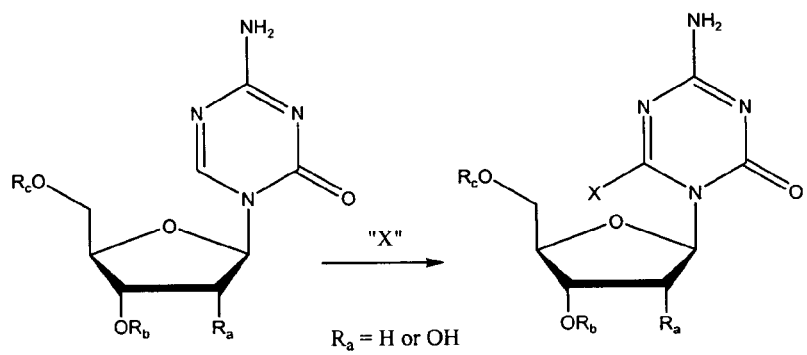
FIG. 7C illustrates a synthetic scheme for halogenation of the triazine ring of decitabine or azacitidine.

Halogenation of the triazine moiety can be performed by modifying pre-existing procedures. One such procedure is reaction of anodically generated "halonium (X)" ions with protected decitabine or azacitidine (FIG. 7C) Palminsano, G.; Danieli, B;

Santagostino, M.; Vodopivec, B. *Tetrahedron Lett.* 1993, 33, 7779–7782. Another is to treat protected decitabine or azacitidine with strong bases such as lithium and sodium hydride or alkyl lithium such as butyl tert-butyl lithium to generate an anion to react with electrophilic halogenating agents such as $(CF_3SO_2)_2NF$ and Selectfluor™ (Barnette, W. E. *J. Am. Chem. Soc.* 1984,106, 452–454.), $Br_2$ (Schwartz, E. B.; Knobler, C. B.; Cram, D. *J. J. Am. Chem. Soc.* 1992, 114, 10775–10784), and $I_2$ (Tsang, Y. K.; Diaz, H.; Graciani, N.; Kelly, J. W. *J. Am. Chem. Soc.,* 1994, 116, 3988–4005) to form halogen-substitution at the 6-position on the triazine ring. From the 6-iodo derivative, interconversion to into 6-fluoro (Lee, S. H.; Swartz, J. *J. Am. Chem. Soc.;* 1986, 108, 2445–2447), chloro and bromo (Commercon, A.; Normant, J.; Villieras, J. *J. Organometallic Chem.* 1975, 93, 415–421) derivatives is possible.

Figure 7D:
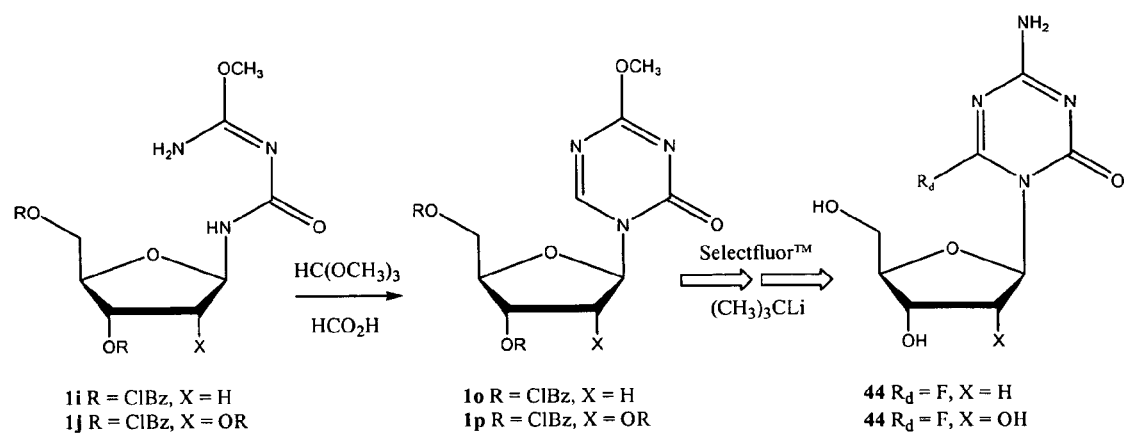
FIG. 7D illustrates a scheme for synthesis of 6-fluoride derivatives of decitabine or azacitidine.

In one embodiment, for example, azacytidine derivative 44 was prepared by stirring and refluxing (~90° C.) a mixture of 1'-(2'-Deoxy-3', 5'-di-O-p-chlorobenzoyl-D-ribofuranosyl)-4-O-methylisobiruet (1i) in formic acid (1.5 eq.) and 50 equivalents of trimethyl orthoformate until complete reaction (<5% 1i remaining) as determined by HPLC. The reaction was cooled to 22±5° C. before charging slowly (in a period of not less than 2 hours) with water (not less than 3 kg of water per mole of 1i used) to precipitate the fully protected intermediate (FIG. 7D). The mixture was stirred for an additional one hour before it was cooled to 5±5° C. and stirred for two hours. The slurry was filtered and the solid cake was dried in vacuo at 50±5° C. until loss on drying (LOD) was less than 0.1%. The protected intermediate (1o) was dissolved (0.001 to 10 M concentration) in an anhydrous aprotic organic solvent effective in solubilizing it. These solvents include, but are not limited to: acetonitrile; chlorobenzene; dichloromethane; 1,2-dichloroethane; methylcyclohexane; N-methylpyrrolidone; nitromethane; acetone; DMSO; ethyl acetate; ethyl ether; and ethyl formate. While the reaction mixture was submerged in a bath (−78 to 20° C.), a slight excess of tert-butyllithium solution in pentane was slowly added (a period of not less than 30 minutes) before an electrophilic fluorinating agent such as Selectfluor™ (1.1 to 10 eq.) was added. The reaction mixture was stirred until complete reaction as determined by HPLC (<5% 1o remaining) or TLC. The reaction mixture was diluted with the solvent, washed with cold saturated ammonium chloride, the organic layer dried with sodium or magnesium sulfate (until no clumps form), filtered, concentrated, and dried in vacuo at not more than 50° C. until loss on drying (LOD) was less than 0.1%. The dried intermediate was suspended in a mixture of anhydrous methanol (~21 liters per mole of intermediate used) and anhydrous ammonia gas (~22 eq.), and the mixture was stirred for not less than 48 hours and until complete consumption of intermediate product. After reaction completion excess ammonia was removed by application of a slight vacuum for one hour before the mixture was concentrated in vacuo at 50±5° C. to a minimal volume (~6 liters per mole of intermediate used) and cooled to 5±5° C. initiate crystallization of the crude product. The crude product was filtered after 1 hour, washed with cold (5° C.) methanol (0.5 liter per mole of intermediate used), dissolved in hot (42° C.) anhydrous methanol (33 liters per mole of intermediate used), decolorized with activated carbon (equivalent to 24 g per mole of intermediate used), filtered to obtain a clear solution of product, concentrated in vacuo at not more than 50° C. to a minimal volume (~2 liters per mole of intermediate used), and allowed to crystallize at 22±5° C. for ~12 hours. The slurry was filtered, the crystalline product washed with methanol (0.2 liter per mole of intermediate used), and the pure product 44 (FIG. 7D, where $R_d$=F and X=H) dried in vacuo at not more than 40° C. for 8 hours.

Azacitidine derivative 44 (FIG. 7D, where $R_d$=F and X=OH) can likewise be synthesized starting from 1'-(2',3', 5'-tri-O-p-chlorobenzoyl-D-ribofuranosyl)-4-O-methylisobiruet (1i).

The sequence of incorporation of the functional groups can be determined by one of ordinary skill in the art based on the yield and efficiency of the reactions.

4. Alkyl-Halogen Derivatives of Decitabine or Azacitidine

Figure 8A:
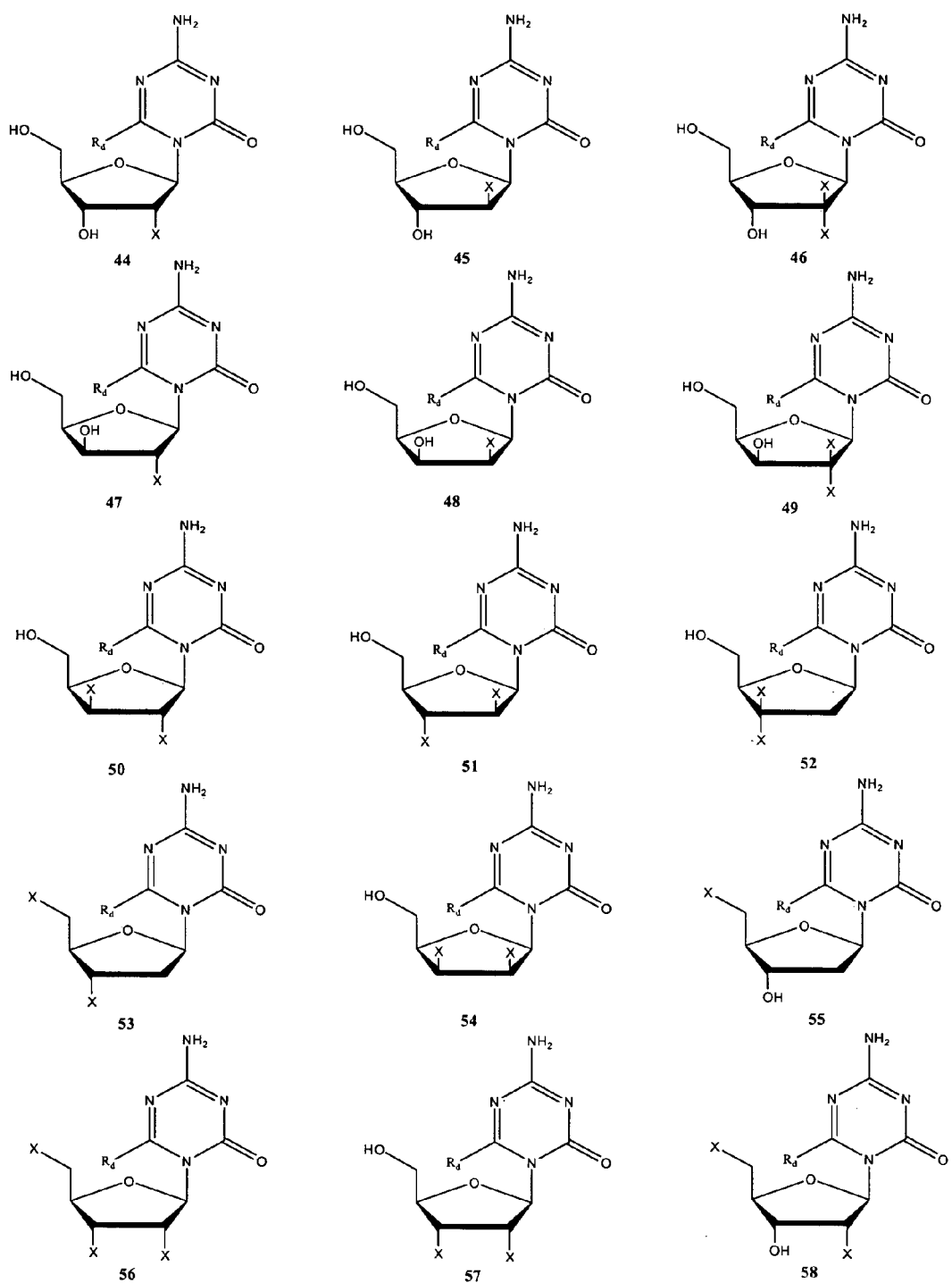
FIGS. 8A–B illustrate examples of decitabine and azacitidine derivatives with combined modifications at the 6-position and at the 2', 3' and/or 5' position.
Figure 8B:
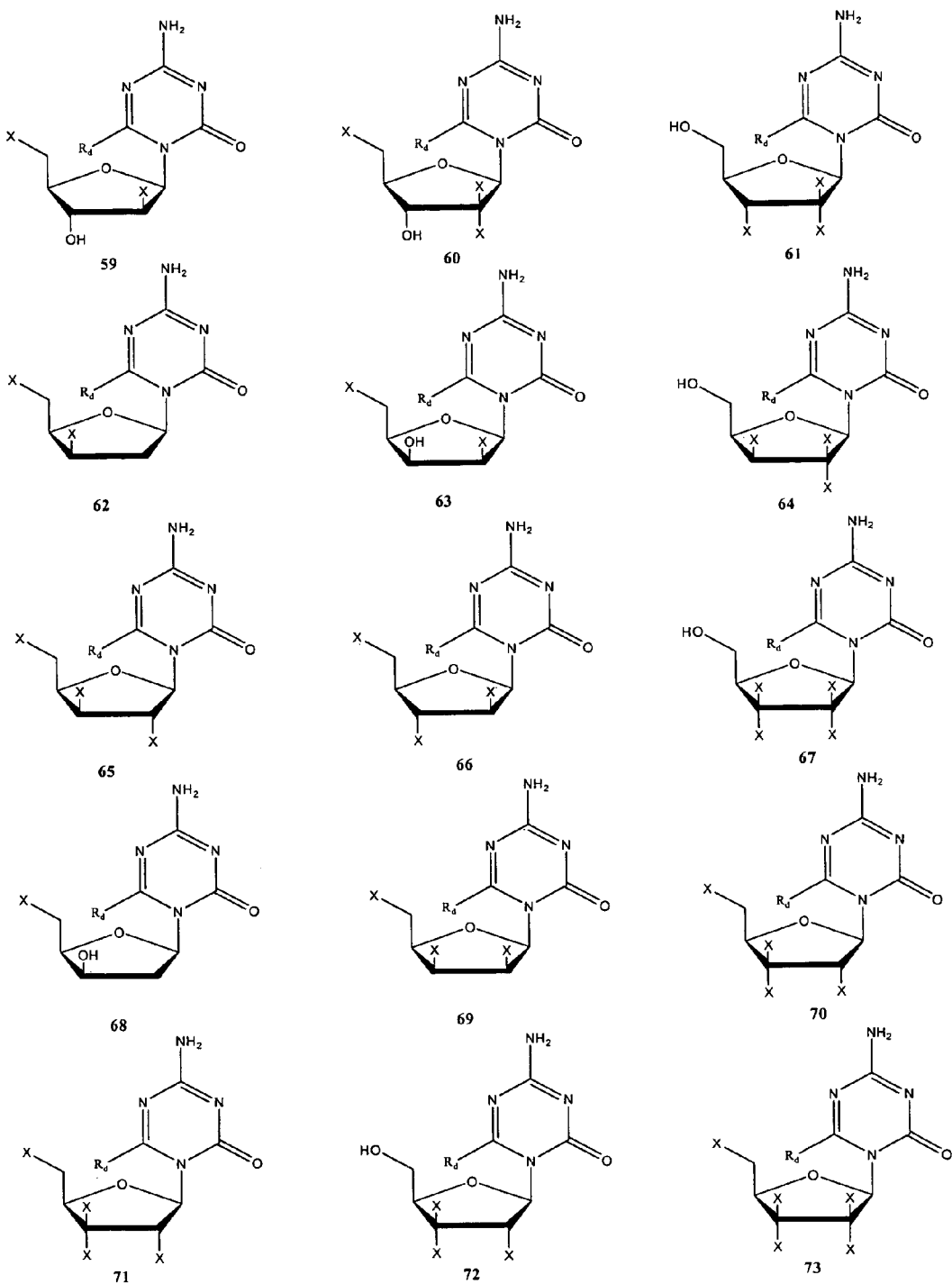

FIGS. 8A, B, D, E, F, G list preferred examples of decitabine and azacitidine derivatives with combined modifications at the 4- or 6-position and at the 2',3' and/or 5' position. The inventors believe that combining modifications on the triazine and ribose ring should stabilize the derivatives and render them more resistant to hydrolytic cleavages than those with modification on the triazine or ribose ring alone.

Figure 8C:
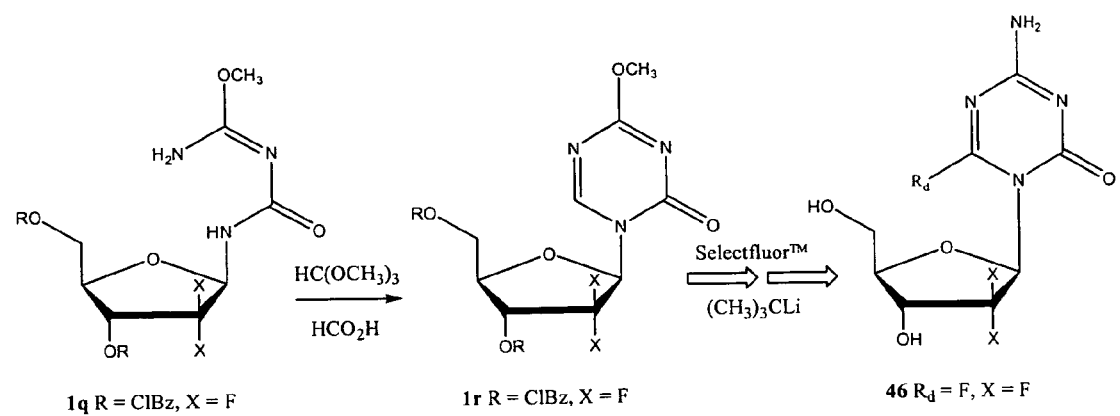
FIG. 8C illustrates a scheme for synthesis of an analogous fluoro-intermediate.
Figure 8D:
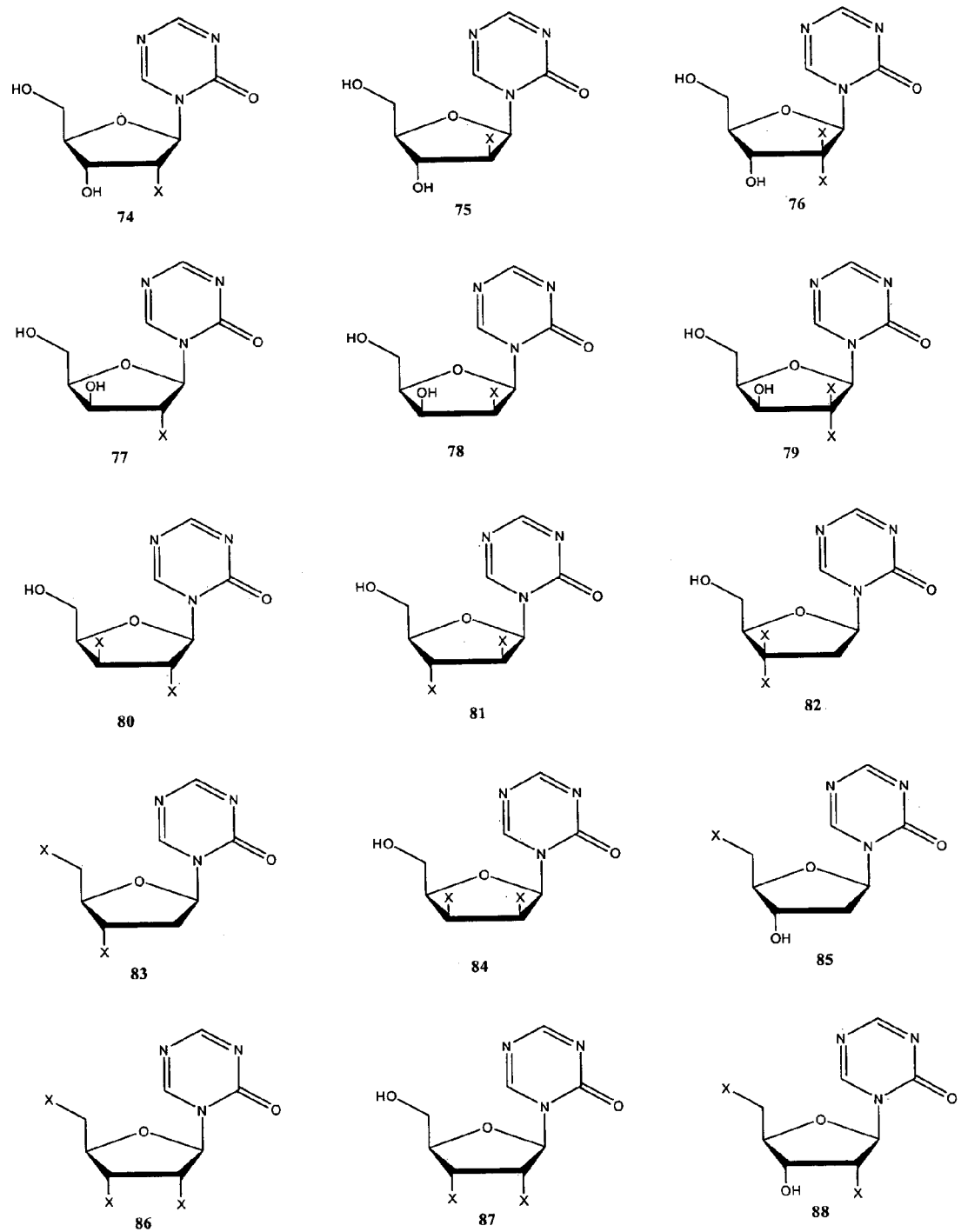
FIGS. 8D–G illustrate examples of decitabine and azacitidine derivatives with combined modifications at the 4-position and at the 2', 3' and/or 5' position.
Figure 8E:
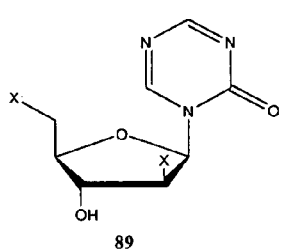
Figure 8E:
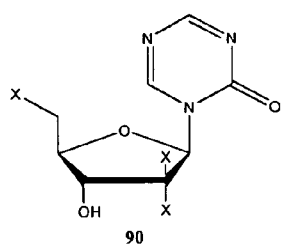
Figure 8E:
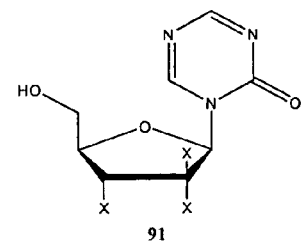
Figure 8E:
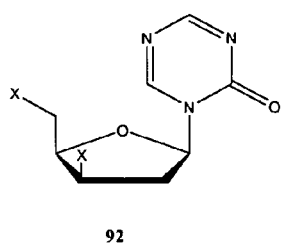
Figure 8E:
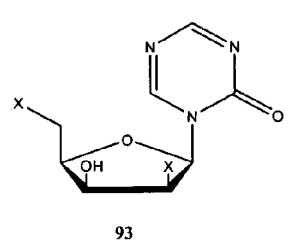
Figure 8E:
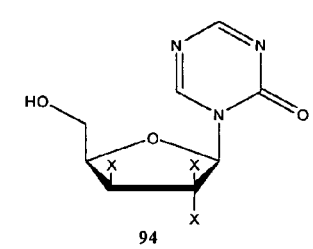
Figure 8E:
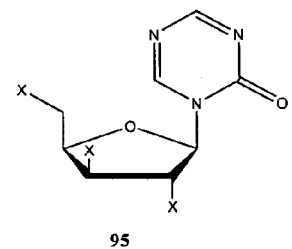
Figure 8E:
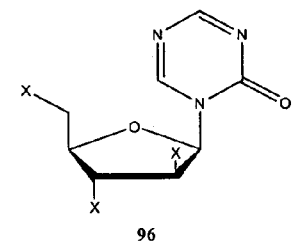
Figure 8E:
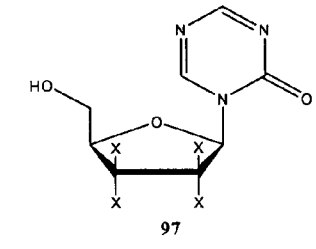
Figure 8E:
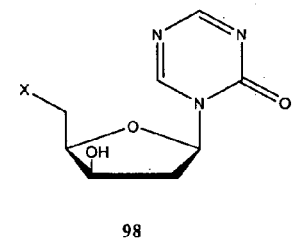
Figure 8E:
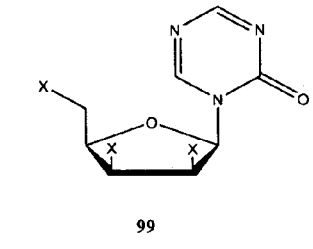
Figure 8E:
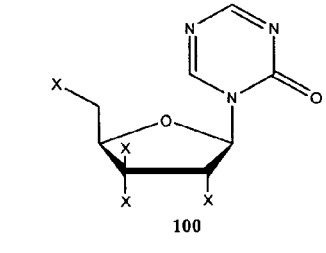
Figure 8E:
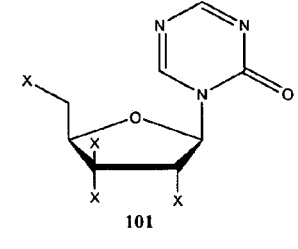
Figure 8E:
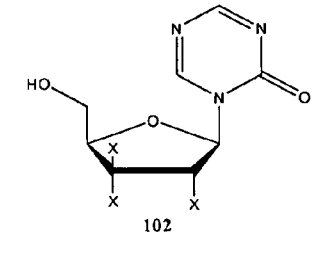
Figure 8E:
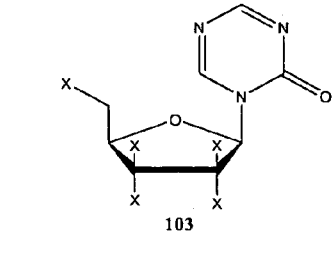
Figure 8F:
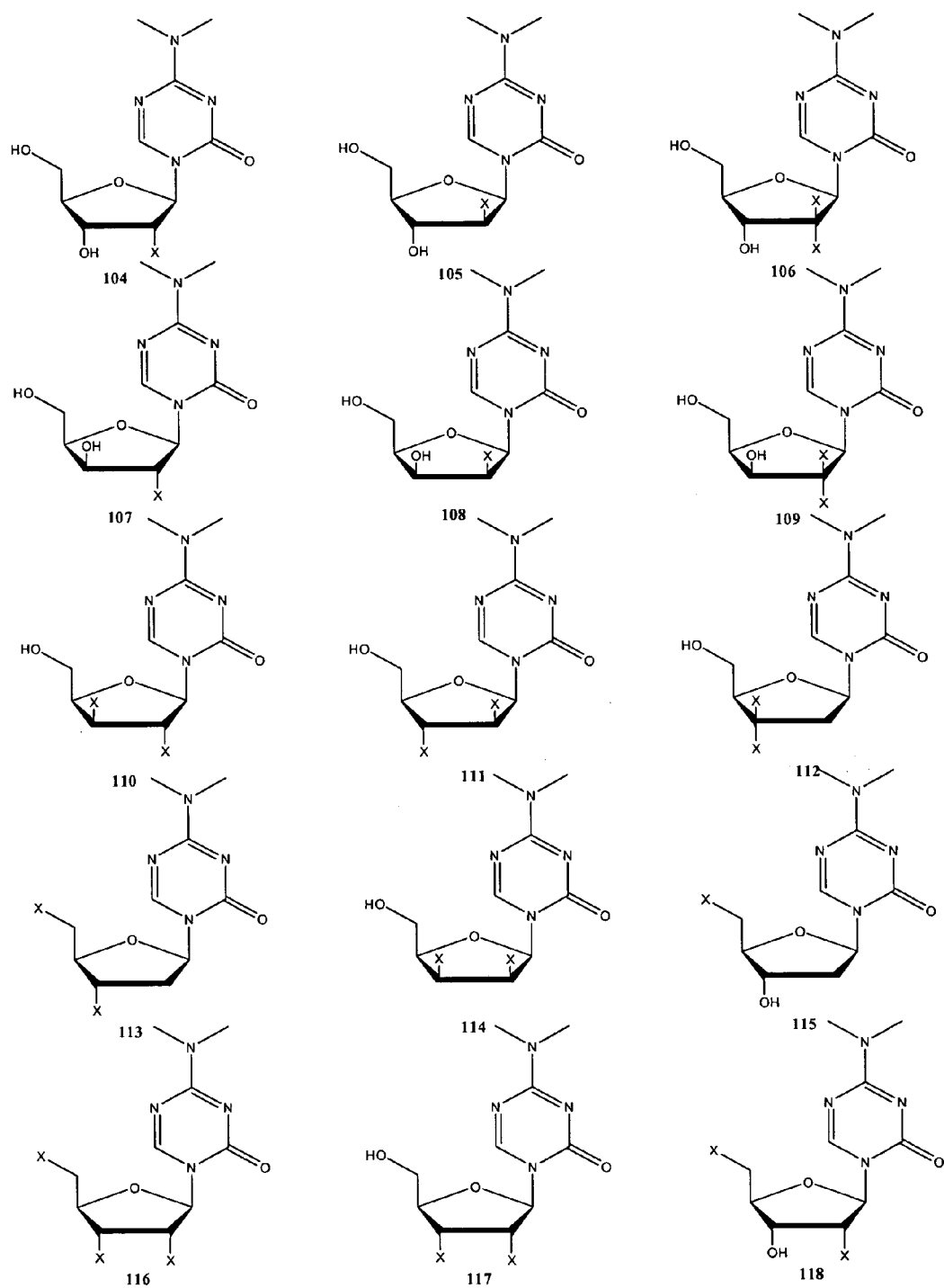
Figure 8G:
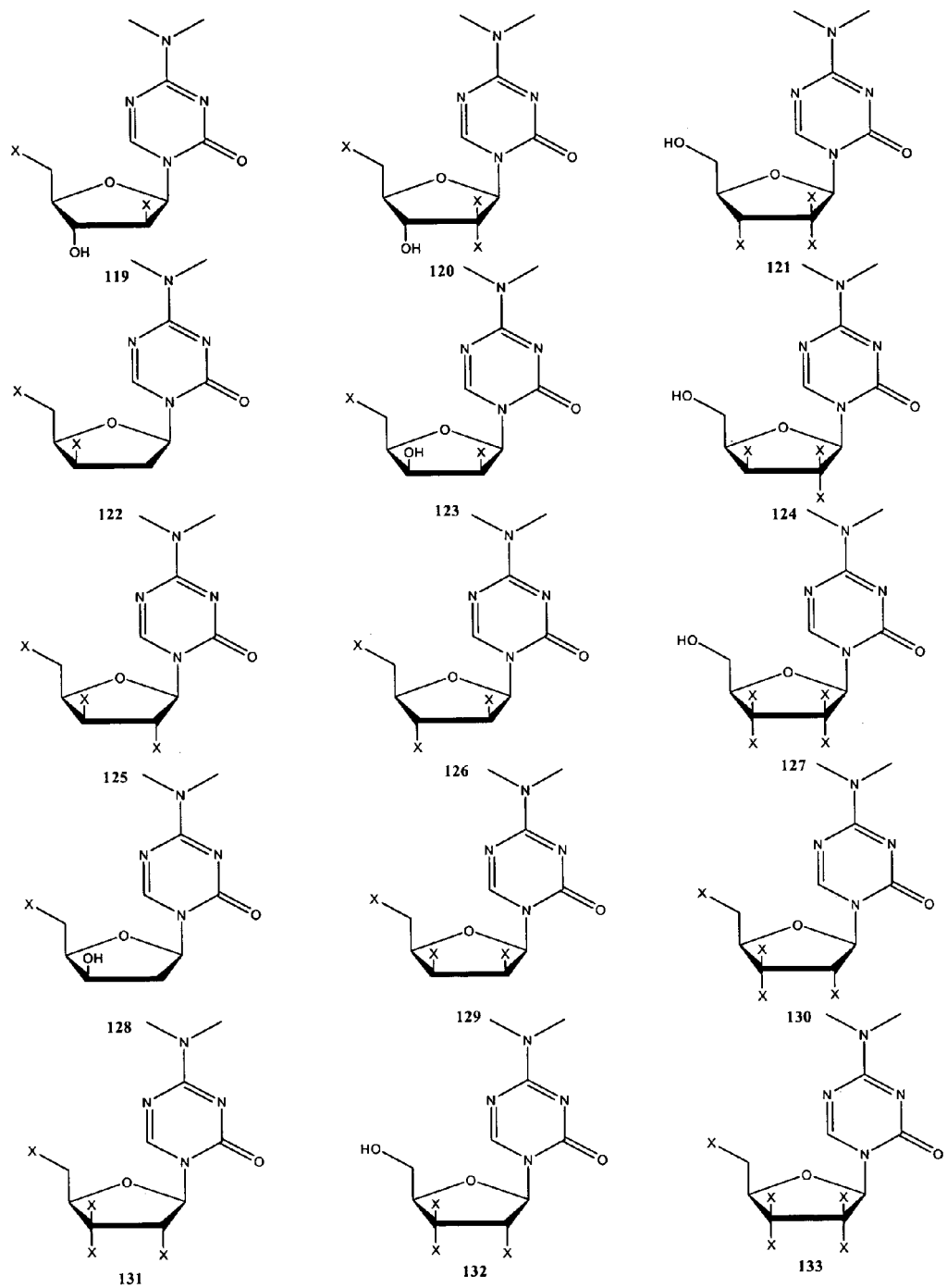

The procedure used to synthesize 1i and 1j can be adapted to prepare an analogous fluoro-intermediate 1q (FIG. 8C), from which subsequent fluoro derivative 46 can be synthesized. Likewise, other fluoro-intermediates are accessible.

In one embodiment, for example, azacytidine derivative 46 was prepared by stirring and refluxing (~90° C.) a mixture of 1'-(2'-deoxy-3',5'-di-O-p-chlorobenzoyl-2',2'-difluoro-D-ribofuranosyl)-4-O-methylisobiruet (1q) in formic acid (1.5 eq.) and 50 equivalents of trimethyl orthoformate until complete reaction (<5% 1q remaining) as determined by HPLC. The reaction was cooled to 22±5° C. before charging slowly (in a period of not less than 2 hours) with water (not less than 3 kg of water per mole of 1q used) to precipitate the fully protected intermediate (1r, FIG. 8C). The mixture was stirred for an additional one hour before it was cooled to 5±5° C. and stirred for two hours. The slurry was filtered and the solid cake was dried in vacuo at 50±5° C. until loss on drying (LOD) was less than 0.1%. The protected intermediate (1r) was dissolved (0.001 to 10 M concentration) in an anhydrous aprotic organic solvent effective in solubilizing it. These solvents include, but are not limited to: acetonitrile; chlorobenzene; dichloromethane; 1,2-dichloroethane; methylcyclohexane; N-methylpyrrolidone; nitromethane; acetone; DMSO; ethyl acetate; ethyl ether; and ethyl formate. While the reaction mixture was submerged in a bath (−78 to 20° C.), a slight excess of tert-butyllithium solution in pentane was slowly added (a period of not less than 30 minutes) before an electrophilic fluorinating agent such as Selectfluor™ (1.1 to 10 eq.) was added. The reaction mixture was stirred until complete reaction as determined by HPLC (<5% 1r remaining) or TLC. The reaction mixture was diluted with the solvent, washed with cold saturated ammonium chloride, the organic layer dried with sodium or magnesium sulfate (until no clumps form), filtered, concentrated, and dried in vacuo at not more than 50° C. until loss on drying (LOD) was less than 0.1%. The dried intermediate was suspended in a mixture of anhydrous methanol (~21 liters per mole of intermediate used) and anhydrous ammonia gas (~22 eq.), and the mixture was stirred for not less than 48 hours and until complete consumption of intermediate product. After reaction completion excess ammonia was removed by application of a slight vacuum for one hour before the mixture was concentrated in vacuo at 50±5° C. to a minimal volume (~6 liters per mole of intermediate used) and cooled to 5±5° C. to initiate crystallization of the crude product. The crude product was filtered after 1 hour, washed with cold (5° C.) methanol (0.5 liter per mole of intermediate used), dissolved in hot (42° C.) anhydrous methanol (33 liters per mole of intermediate used), decolorized with activated carbon (equivalent to 24 g per mole of intermediate used), filtered to obtain a clear solution of product, concentrated in vacuo at not more than 50° C. to a minimal volume (~2 liters per mole of intermediate used), and allowed to crystallize at 22±5° C. for ~12 hours. The slurry was filtered, the crystalline product washed with methanol (0.2 liter per mole of intermediate used), and the pure product 46 (FIG. 8C, where $R_d$=H and X=F) dried in vacuo at not more than 40° C. for ~8 hours.

Figure 8H:
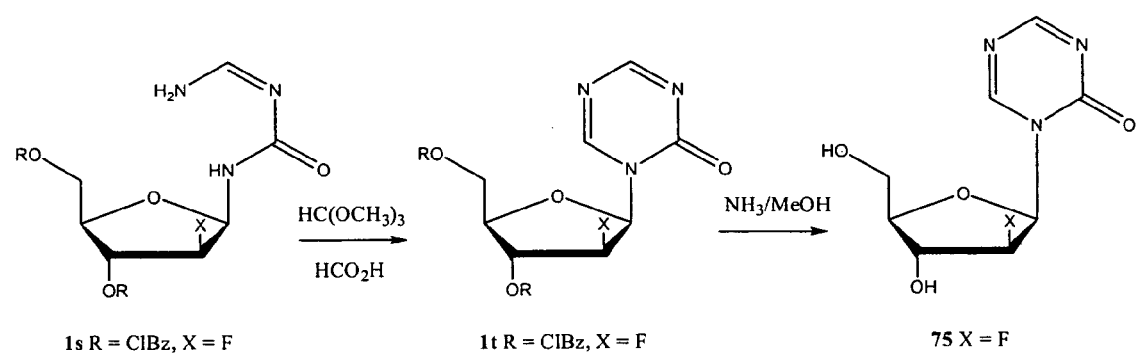
FIG. 8H illustrates a scheme for synthesis of an analogous fluoro-intermediate.

The procedure used to synthesize 1i and 1j can be adapted to prepare an analogous fluoro-intermediate 1s (FIG. 8H), from which subsequent fluoro derivatives 1t and 75 can be synthesized. Likewise, other fluoro-intermediates are accessible.

While the present invention is disclosed with reference to preferred embodiments detailed above, it is to be understood that these embodiments are intended in an illustrative or exemplary rather than in a limiting sense, as it is contemplated that modifications will readily occur to those skilled in the art, modifications which will be within the spirit of the invention and the scope of the appended claims. All patents, papers, articles, references and books cited herein are incorporated by reference in their entirety.

What is claimed is:

1. A compound of Formula I,

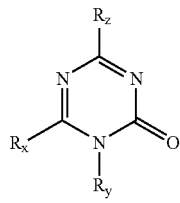

I or its pharmaceutically acceptable salt, wherein
$R_x$ is hydrogen, halogen, substituted or unsubstituted alkyl, substituted or unsubstituted aryl, halogen-substituted alkyl or aryl, phenyl, benzyl, hydroxyl, thiol, substituted or unsubstituted amino, —O-alkyl, —S-alkyl, —O-aryl or —S-aryl;
$R_y$ is alkyl, or substituted or unsubstituted ribose or 2'-deoxyribose; and
$R_z$ is a hydrogen, aryl, arylalkyl, amino, dialkylamino, alkylarylamino, hydrazine, hydroxylalkylamino, —O-alkyl, —S-alkyl, —O-aryl or —S-aryl, provided that when $R_x$ is phenyl or benzyl, and $R_y$ is ribose or 2'-deoxyribose, $R_z$ is not amino or dimethylamino.

2. The compound or its pharmaceutically acceptable salt according to claim 1, wherein $R_x$ is mono-, di- or trifluoromethyl.

3. The compound or its pharmaceutically acceptable salt according to claim 1, wherein $R_x$ is a straight or branched chain $C_{1-6}$ alkyl.

4. The compound or its pharmaceutically acceptable salt according to claim 1, wherein $R_x$ is selected from the group consisting of methyl, ethyl, propyl, butyl and phenyl.

5. The compound or its pharmaceutically acceptable salt according to claim 1, wherein $R_x$ is fluoride.

6. The compound or its pharmaceutically acceptable salt according to claim 1, wherein $R_x$ is chloride or bromide.

7. The compound or its pharmaceutically acceptable salt according to claim 1, wherein $R_x$ is primary or secondary amino.

8. The compound or its pharmaceutically acceptable salt according to claim 1, wherein $R_x$ is halogen, and $R_z$ is amino.

9. The compound or its pharmaceutically acceptable salt according to claim 1, wherein $R_x$ is fluoride, and $R_z$ is amino.

10. The compound or its pharmaceutically acceptable salt according to claim 1, wherein the $R_x$ is alkyl, and $R_y$ is $OCH_3$ or O-alkyl.

11. The compound or its pharmaceutically acceptable salt according to claim 1, wherein the Rx is alkyl, $R_y$ is 2'-deoxyribose and $R_z$ is dimethylamino.

12. The pharmaceutically acceptable salt of the compound according to claim 1, wherein the salt is selected from the group consisting of hydrochloride, mesylate, EDTA, sulfite, L-Aspartate, maleate, phosphate, L-Glutamate, (+)-L-Tartrate, citrate, L-Lactate, succinate, acetate, hexanoate, butyrate, and propionate salt.

13. The compound according to claim 1 having a structure of Formula IV

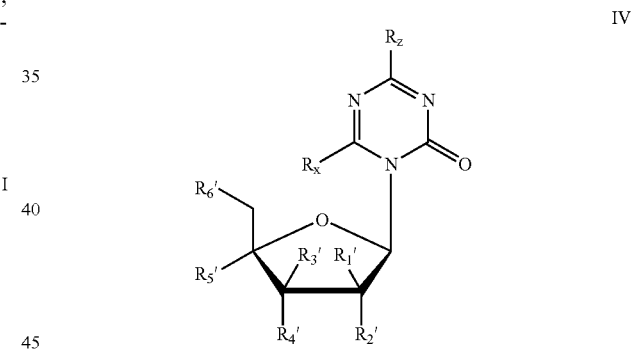

IV or its pharmaceutically acceptable salt, wherein each of $R_1'$, $R_2'$, $R_3'$, $R_4'$, $R_5'$, and $R_6'$ is independently selected from the group consisting of hydrogen, hydroxyl, fluoride, choloride, bromide, iodide, $CF_3$, —O-alkyl, —O-acyl, —O-aryl, —S-alkyl, and —S-aryl, provided that when $R_x$ is hydrogen and $R_z$ is amino, $R_4'$ is not hydroxyl.

14. The compound or its pharmaceutically acceptable salt according to claim 13, wherein $R_4'$ is hydrogen; and each of $R_1'$, $R_2'$, $R_3'$, $R_5'$, and $R_6'$ is independently selected from the group consisting of hydrogen, hydroxyl, fluoride, chloride, bromide, iodide, $CF_3$, —O-alkyl, —O-acyl, —O-aryl, —S-alkyl, and —S-aryl.

15. The pharmaceutically acceptable salt of the compound according to claim 13, wherein the salt is selected from the group consisting of hydrochloride, mesylate, EDTA, sulfite, L-Aspartate, maleate, phosphate, L-Glutamate, (+)-L-Tartrate, citrate, L-Lactate, succinate, acetate, hexanoate, butyrate, and propionate salt.

16. A pharmaceutical composition comprising a therapeutically-effective amount of an active compound and a pharmaceutically-acceptable carrier, said active compound being a compound according to claim 1 or its pharmaceutically acceptable salt.

17. The pharmaceutical composition according to claim 16, wherein the pharmaceutically-acceptable carrier is an aqueous solution.

18. The pharmaceutical composition according to claim 17, wherein the aqueous solution comprises a water miscible non-aqueous solvent selected from the group consisting of glycerin, propylene glycol, polyethylene glycol, and combinations thereof.

19. The pharmaceutical composition according to claim 17, wherein the amount of the active compound in the composition is between 0.1 and 200 mg per ml of the aqueous solution.

20. The pharmaceutical composition according to claim 16, wherein the pharmaceutical carrier is a solution comprising less than 40% water and a water miscible non-aqueous solvent.

21. The pharmaceutical composition according to claim 16, wherein the non-aqueous solvent is selected from the group consisting of glycerin, propylene glycol, polyethylene glycol, and combinations thereof.

22. The pharmaceutical composition according to claim 16, wherein the pharmaceutical carrier is a solution comprising less than 20% water and a water miscible non-aqueous solvent.

23. The pharmaceutical composition according to claim 16, being in a form of lyophilized powder.

24. The pharmaceutical composition according to claim 16, further comprising an acidifying agent added to the composition in a proportion such that the composition has a resulting pH between about 4 and 8.

25. The pharmaceutical composition according to claim 24, wherein the acidifying agent is an inorganic or organic acid.

26. The pharmaceutical composition according to claim 25, wherein the organic acid is selected from the group consisting of ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid.

27. The pharmaceutical composition according to claim 25, wherein the inorganic acid is selected from the group consisting of hydrochloric acid, sulphuric acid, phosphoric acid, and nitric acid.

28. The pharmaceutical composition according to claim 25, wherein the acidifying agent is ascorbic acid.

29. The pharmaceutical composition according to claim 16, further comprising a pharmaceutically acceptable excipient.

30. The pharmaceutical composition according to claim 29, wherein the excipient is selected from the group consisting of mannitol, sorbitol, lactose, dextrox, and cyclodextrin.

31. The pharmaceutical composition according to claim 30, wherein the cyclodextrin is α-, β-, or γ-cyclodextrin.

32. The pharmaceutical composition according to claim 30, the cyclodextrin is a modified, amorphous cyclodextrin selected from the group consisting of hydroxypropyl-, hydroxyethyl-, glucosyl-, maltosyl-, maltotriosyl-, carboxyamidomethyl-, carboxymethyl-, sulfobutylether-, and diethylamino-substituted α-, β-, and γ-cyclodextrin.

33. The pharmaceutical composition according to claim 16, wherein at least 80% of the active compound remains in active form after storage at 25° C. for 7 days.

34. The pharmaceutical composition according to claim 16, wherein at least 80% of the active compound remains in active form after storage at 25° C. for 14 days.

35. The pharmaceutical composition according to claim 16, wherein at least 80% of the active compound remains in active form after storage at 40° C. for 7 days.

36. The pharmaceutical composition according to claim 30, further comprising: a therapeutic agent selected from the group consisting of anti-neoplastic agents, alkylating agents, agents that are members of the retinoids superfamily, hormonal agents, plant-derived agents, biologic agents, interleukins, interferons, cytokines, immuno-modulating agents, and monoclonal antibodies.

37. A kit, comprising:
a first vessel containing a compound according to claim 1 or its pharmaceutically acceptable salt in a solid form.

38. The kit according to claim 37, wherein the active compound is in a form of lyophilized powder.

39. The kit according to claim 38, further comprising:
a second vessel containing a diluent comprising glycerin, propylene glycol, polyethylene glycol or combinations thereof.

40. The kit according to claim 39, wherein the diluent comprises less than 40% water in volume.

41. The kit according to claim 37, where the amount of active compound in the first vessel is between 0.1 and 200 mg.

42. The kit according to claim 37, wherein the diluent further comprises an acidifying agent.

43. The kit according to claim 37, further comprising: a written instruction describing how to administer the active compound as a pharmaceutical to a patient.

* * * * *

UNITED STATES PATENT AND TRADEMARK OFFICE
CERTIFICATE OF CORRECTION

| | | |
|---|---|---|
| PATENT NO. | : 7,250,416 B2 | Page 1 of 1 |
| APPLICATION NO. | : 11/077862 | |
| DATED | : July 31, 2007 | |
| INVENTOR(S) | : Pasit Phiasivongsa et al. | |

It is certified that error appears in the above-identified patent and that said Letters Patent is hereby corrected as shown below:

Column No. 37, Line No. 21, please change "16" to --20--.

Column No. 38, Line No. 23, please change "30" to --16--.

Signed and Sealed this

Sixth Day of November, 2007

JON W. DUDAS
*Director of the United States Patent and Trademark Office*